United States Patent [19]
MacCoss et al.

[11] Patent Number: 5,610,165
[45] Date of Patent: Mar. 11, 1997

[54] N-ACYLPIPERIDINE TACHYKININ ANTAGONISTS

[75] Inventors: Malcolm MacCoss, Freehold; Sander G. Mills, Woodbridge, both of N.J.

[73] Assignee: Merck & Co., Inc., Rahway, N.J.

[21] Appl. No.: 198,025

[22] Filed: Feb. 17, 1994

[51] Int. Cl.$^6$ .................... A61K 31/445; C07D 211/06
[52] U.S. Cl. .................... 514/315; 514/325; 546/226
[58] Field of Search .................... 514/315; 546/226

[56] References Cited

U.S. PATENT DOCUMENTS

| | | | |
|---|---|---|---|
| 4,804,661 | 2/1989 | Ferrini et al. | 514/255 |
| 5,019,576 | 5/1991 | Braquet et al. | 514/255 |
| 5,064,838 | 11/1991 | Carr et al. | 514/317 |
| 5,292,726 | 3/1994 | Ashton et al. | 514/85 |

FOREIGN PATENT DOCUMENTS

| | | |
|---|---|---|
| 0343900 | 11/1989 | European Pat. Off. . |
| 0436334 | 7/1991 | European Pat. Off. . |
| 0499313 | 8/1992 | European Pat. Off. . |
| 0528495 | 2/1993 | European Pat. Off. . |
| 0532456 | 3/1993 | European Pat. Off. . |
| 0533280 | 3/1993 | European Pat. Off. . |
| 0559538 | 9/1993 | European Pat. Off. . |
| WO92/06079 | 4/1992 | WIPO . |
| WO92/12128 | 7/1992 | WIPO . |
| WO93/01170 | 1/1993 | WIPO . |
| WO93/14084 | 7/1993 | WIPO . |
| WO94/00440 | 1/1994 | WIPO . |
| WO94/03445 | 2/1994 | WIPO . |

OTHER PUBLICATIONS

Lowe, et al., "The Discovery of (2S, 3S)-cis-2-(Diphenylmethyl)-N-[(2-methoxphenyl)methyl]-2-azabicyclo[2.2.2.]-octan-3-amine...", *J. Med. Chem.* 35, pp. 2591–2600 (1992).

Lowe, et al., "Substance P Antagonists", *Drug News Perspect.*, 5(4), pp. 223–227, (1992).

Mills, et al., "1,4-Diacylpiperazine-2-(S)-[(N-Aminoalkyl) Carboxamides], as Novel, . . .", *Bioorganic & Medicinal Chemistry Letters*, 3(12), pp. 2707–2712, (1993).

*Primary Examiner*—Amelia A. Owens
*Attorney, Agent, or Firm*—J. Eric Thies; David L. Rose

[57] ABSTRACT

N-Acylpiperidines of general structure

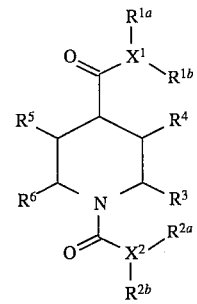

are tachykinin receptor antagonists useful in the treatment of inflammatory diseases, pain or migraine, asthma and emesis.

10 Claims, No Drawings

N-ACYLPIPERIDINE TACHYKININ ANTAGONISTS

SUMMARY OF THE INVENTION

This invention is concerned with novel compounds represented by structural formula I:

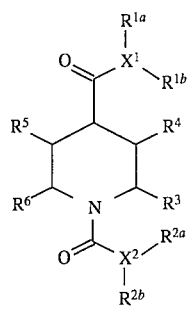

wherein $X^1$, $X^2$, $R^{1a}$, $R^{1b}$, $R^{2a}$, $R^{2b}$, $R^3$, $R^4$, $R^5$, and $R^6$ are hereinafter defined.

The invention is also concerned with pharmaceutical formulations with these novel compounds as active ingredients and the use of the novel compounds and their formulations in the treatment of certain disorders.

The compounds of this invention have activity as tachykinin receptor antagonists and are useful in the treatment of inflammatory diseases, pain or migraine, asthma and emesis.

Also, some of these compounds are calcium channel blockers and are useful in the treatment of cardiovascular disorders such as angina, hypertension or ischemia.

BACKGROUND OF THE INVENTION

Analgesia has historically been achieved in the central nervous system by opiates and analogs which are addictive, and peripherally by cyclooxygenase inhibitors that have gastric side effects. Substance P antagonists may induce analgesia both centrally and peripherally. In addition, substance P antagonists are inhibitory of neurogenic intimation.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and mictrition (B. Pernow, *Pharmacol. Rev.,* 1983, 35, 85–141 ). The NK1 and NK2 receptor subtypes are implicated in synaptic transmission (Laneuville et al., *Life Sci.,* 42:1295–1305 (1988)).

The receptor for substance P is a member of the superfamily of G protein-coupled receptors. This superfamily is an extremely diverse group of receptors in terms of activating ligands and biological functions. In addition to the tachykinin receptors, this receptor superfamily includes the opsins, the adrenergic receptors, the muscarinic receptors, the dopamine receptors, the serotonin receptors, a thyroid-stimulating hormone receptor, a luteinizing hormone-chorionogonadotropic hormone receptor, the product of the oncogene ras, the yeast mating factor receptors, a *Dictyostelium* cAMP receptor, and receptors for other hormones and neurotransmitters (see A. D. Hershey, et al., *J. Biol. Chem.,* 1991, 226, 4366–4373).

Substance P (also called "SP" herein) is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence Phe-X-Gly-Leu-Met-$NH_2$. In addition to SP the known mammalian tachykinins include neurokinin A and neurokinin B. The current nomenclature designates the receptors for SP, neurokinnin A, and neurokinin B as NK-1, NK-2, and NK-3, respectively.

More specifically, substance P is a pharmacologically-active neuropeptide that is produced in mammals and possesses a characteristic amino acid sequence (Chang et al., *Nature New Biol.* 232, 86 (1971); D. F. Veber et al., U.S. Pat. No 4,680,283).

Substance P acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., *Science,* 199, 1359 (1978); P. Oehme et al., *Science,* 208, 305 (1980)) and plays a role in sensory transmission and pain perception (T. M. Jessell, *Advan. Biochem. Psychopharmacol.* 28, 189 (1981 )). For example, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (Dec. 1987) 8 506–510]. In particular, substance P has been shown to be involved in the transmission of pain in migraine (see B. E. B. Sandberg et al., *Journal of Medicinal Chemistry,* 25, 1009 (1982)), and in arthritis (Levine et al. *Science,* (1984) 226 547–549). These peptides have also been implicated in gastrointestinal (GI) disorders and diseases of the GI tract, such as inflammatory bowel disease, ulcerative colitis and Crohn's disease, etc. (see Mantyh et al., *Neuroscience,* 25 (3), 817–37 (1988) and D. Regoli in "Trends in Cluster Headache" Ed. F. Sicuteri et al., Elsevier Scientific Publishers, Amsterdam, 1987, pp. 85–95).

Substance P may play a role in a neurogenic mechanism for arthritis (Kidd et al., "A Neurogenic Mechanism for Symmetric Arthritis" in The Lancet, 11 Nov. 1989 and Gronblad et al., "Neuropeptides in Synovium of Patients with Rheumatoid Arthritis and Osteoarthritis" in *J. Rheumatol.* (1988) 15(12) 1807–10). Therefore, substance P may be involved in the inflammatory response in diseases such as rheumatoid arthritis and osteoarthritis (O'Byme et al., in Arthritis and Rheumatism (1990) 33 1023–8).

Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitus, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyperreflexia is reviewed in "Tachykinin Receptors and Tachykinin Receptor Antagonists," C. A. Maggi, R. Patacchini, P. Rovero and A. Giachetti, *J. Auton. Pharmacol,* (1993) 13, 23–93. Neurokinin-1 receptor antagonists alone or in combination with bradykinin receptor antagonists may also be useful in the prevention and treatment of inflammatory conditions in the lower urinary tract, especially cystitis (Giuliani, et al., *J. Urology*, 150, 1014–1017 (1993)). Other disease areas where tachykinin antagonists are believed to be useful are allergic conditions (Hamelet et al., Can. *J. Pharmacol. Physiol.* (1988) 66 1361–7), immunoregulation (Lotz et al., *Science* (1988) 241 1218–21, Kimball et al., *J. Immunol.* (1988) 141 (10) 3564–9 and A. Perianin, et al., *Biochem, Biophys. Res Commun.* 161, 520 (1989)) vasodilation, bronchospasm, reflex or neuronal control of the viscera (Mantyh et al., PNAS (1988) 85 3235–9) and, possibly by arresting or slowing β-amyloid-mediated neurodegenerative changes (Yankner et al., *Science*, (1990) 250, 279–82) in senile dementia of the Alzheimer type, Alzheimer's disease and Downs Syndrome. Substance P may also play a role in demyelinating diseases such as multiple sclerosis and amyotrophic lateral sclerosis [J. Luber-Narod et. al., poster presented at C. I. N. P. XVIIIth Congress, 28 1th Jun.-2nd Jul., 1992, in press]. Antagonists selective for the neurokinin-1 (NK-1) and/or the neurokinin-2 (NK-2) receptor may be useful in the treatment of asthmatic disease (Frossard et al., *Life Sci.*, 49, 1941–1953 (1991 ); Advenier, et al., *Biochem. Biophys. Res. Comm.*, 184(3), 1418–1424 (1992)). Tachykinin antagonists may also be useful in the treatment of small cell carcinomas, in particular small cell lung cancer (SCLC) (Langdon et al., Cancer Research (1992) 52, 4554–7).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosis (EPO Publication No. 0,436,334) conjunctivitis, vernal conjunctivitis, contact dermatitis, atropic dermatitis, urticaria, and other eczematoid dermatitis (EPO Publication No. 0,394,989) and emesis (*Trends Pharmacol, Sci.*, 9, 334–341 (1988); *Eur. J. Pharmacol.*, 249, R3–R4 (1993)).

Substance P antagonists may be useful in mediating neurogenic mucus secretion in mammalian airways and hence provide treatment and symptomatic relief in diseases characterized by mucus secretion, in particular, cystic fibrosis [S. Ramnarine, et al., abstract presented at 1993 ALA/ATS Int'l Conference, 16–19 May, 1993, published in Am. Rev. of Respiratory Dis., May 1993, in press].

In the recent past, some attempts have been made to provide peptide-like substances that are antagonists for substance P and other tachykinin peptides in order to more effectively treat the various disorders and diseases listed above. See for example Lowe, *Drugs of the Future*, 17 (12) 1115–1121 (1992) and European patent applications (EPO Publication Nos. 0,347,802, 0,401,177 and 0,412,452) which disclose various peptides as neurokinin A antagonists. Also, PCT Patent Publication WO 93/14113 discloses certain peptides as tachykinin antagonists. In addition, EPO Publication No. 0,336,230 discloses heptapeptides which are substance P antagonists useful in the treatment of asthma. Merck U.S. Pat. No. 4,680,283 also discloses peptidal analogs of substance P.

Certain inhibitors of tachykinins have been described in U.S. Pat. No. 4,501,733, by replacing residues in substance P sequence by Trp residues.

A further class of tachykinin receptor antagonists, comprising a monomeric or dimetic hexa- or heptapeptide unit in linear or cyclic form, is described in GB-A-2216529.

The peptide-like nature of such substances make them too labile from a metabolic point of view to serve as practical therapeutic agents in the treatment of disease. The non-peptidic antagonists of the present invention, on the other hand, do not possess this drawback, as they are expected to be more stable from a metabolic point of view than the previously-discussed agents.

It is known in the an that baclofen (β-(aminoethyl)-4-chlorobenzenepropanoic acid) in the central nervous system effectively blocks the excitatory activity of substance P, but because in many areas the excitatory responses to other compounds such as acetylcholine and glutamate are inhibited as well, baclofen is not considered a specific substance P antagonist. Pfizer WIPO patent applications (PCT Publication Nos. WO 90/05525, WO 90/05729, WO 91/18899, WO 92/12151 and WO 92/12152) and publications (*Science*, 251,435–437 (1991); *Science*, 251,437–439 (1991); *J. Med. Chem.*, 35, 2591–2600 (1992)) disclose 2-arylmethyl-3-substituted amino-quinuclidine derivatives which are disclosed as being useful as substance P antagonists for treating gastrointestinal disorders, central nervous system disorders, inflammatory diseases and pain or migraine. A Glaxo European patent application (EPO Publication No. 0.360.390) discloses various spirolactam-substituted amino acids and peptides which are antagonists or agonists of substance P. A Pfizer WIPO patent application (PCT Publication No. WO 92/06079) discloses fused-ring analogs of nitrogen-containing nonaromatic heterocycles as useful for the treatment of diseases mediated by an excess of substance P. A Pfizer WIPO patent application (PCT Publication No. WO 9/15585 discloses 1-azabicyclo[3.2.2]nonan-3-amine derivatives as substance P antagonists. A Pfizer WIPO patent application (PCT Publication No. WO 93/10073) discloses ethylenediamine derivatives as substance P antagonists. PCT Publication No. WO 93/01169 discloses certain aromatic compounds as tachykinin receptor antagonists. A Sanofi publication (*Life Sci.*, 50, PL101-PL106 (1992)) discloses a 4-phenyl piperidine derivative as an antagonist of the neurokinin A (NK2) receptor.

Howson et al. (*Biorg, & Med. Chem, Lett.*, 2 (6), 559–564 (1992)) disclose certain 3-amino and 3-oxy quinuclidine compounds and their binding to substance P receptors. EPO Publication 0,499,313 discloses certain 3-oxy and 3-thio azabicyclic compounds as tachykinin antagonists. U.S. Pat. No. 3,506,673 discloses certain 3-hydroxy quinuclidine compounds as central nervous system stimulants. A Pfizer EPO Patent application (EPO Publication 0,436,334) discloses certain 3-aminopiperidine compounds as substance P antagonists. U.S. Pat. No. 5,064,838 discloses certain 1,4-disubstituted piperidinyl compounds as analgesics. PCT Publication No. WO 92/12128 discloses certain piperidine and pyrrolidine compounds as analgesics. Peyronel, et al. (*Biorg & Med. Chem, Lett.*, 2 (1), 37–40 (1992)) disclose a fused ring pyrrolidine compound as a substance P antagonist. EPO Publication No. 0,360,390 discloses certain spirolactam derivatives as substance P antagonists. EPO Publication No. 0,532,456 discloses certain 1acylpiperidine derivatives as substance P antagonists. EPO Publication No. 0,559,538 discloses quatemary salts of certain 4-substituted piperidines as neurokinin antagonists. U.S. Pat. No. 4,804, 661 discloses certain piperazine compounds as analgesics. U.S. Pat. No. 4,493,578 discloses certain piperazine compounds useful in the treatment of pain. PCT Publication No. WO 92/01679 discloses certain 1,4-disubstituted piperazines useful in the treatment of mental disorders in which a dopaminergic deficit is implicated. PCT Publication No. WO 92/21360 and Mills, et al. (*Bioorganic & Med. Chem.*

*Lttrs.*, 3(12) 2707–2712 (1993)) disclose certain 1,4-diacylpiperazine substance P receptor antagonists.

DETAILED DESCRIPTION OF THE INVENTION

The novel compounds of this invention are represented by structural formula I:

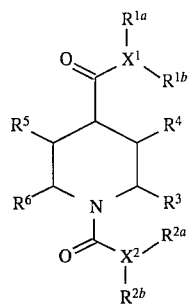

or a pharmaceutically acceptable salt thereof, wherein:

$R^{1a}$ is selected from the group consisting of:
1) H,
2) $C_{1-8}$ alkyl,
3) phenyl, either unsubstituted or substituted with one or two substituents selected from the group consisting of:
   a) —$C_{1-4}$ alkyl,
   b) -halo,
   c) —OH,
   d) —$CF_3$,
   e) —$NH_2$,
   f) —NH($C_{1-4}$ alkyl),
   g) —N($C_{1-4}$ alkyl)($C_{1-4}$ alkyl),
   h) —$CO_2H$,
   i) —$CO_2$($C_{1-4}$ alkyl), and
   j) —$C_{1-4}$ alkoxy;
4) —$C_{1-4}$alkyl-phenyl, wherein the phenyl is either unsubstituted or substituted with one or two substituents selected from:
   a) —$C_{1-4}$ alkyl
   b) -halo,
   c) —OH,
   d) —$CF_3$
   e) —$NH_2$,
   f) —NH($C_{1-4}$ alkyl),
   g) —N($C_{1-4}$ alkyl)
   h) —$CO_2H$,
   i) —$CO_2$(C1-4 alkyl), and
   j) —$C_{1-4}$ alkoxy;

$R^{1b}$ is selected from the group consisting of:
1) $R^{1a}$
2) —$C_{3-7}$ cycloalkyl, and
3) —$CH_2$-$R^{1a}$;

$R^{2a}$ and $R^{2b}$ are independently phenyl, either unsubstituted or substituted with one or two substituents selected from the group consisting of:
1) —$C_{1-4}$ alkoxy,
2) -halo,
3) —OH,
4) —$CF_3$,
5) —$NH_2$,
6) —NH($C_{1-4}$ alkyl),
7) —N($C_{1-4}$ alkyl)$_2$,
8) —$CO_2H$,
9) —$CO_2$($C_{1-4}$ alkyl), and
10) —$C_{1-6}$ alkyl, either unsubstituted or substituted with one or more substituents selected from the group consisting of:
   a) -halo,
   b) —OH,
   c) —$CF_3$,
   d) —$NH_2$,
   e) —NH($C_{1-4}$ alkyl),
   f) —N($C_{1-4}$ alkyl)($C_{1-4}$ alkyl)
   g) —$CO_2H$,
   h) —$CO_2$($C_{1-4}$ alkyl),
   i) $C_{1-4}$alkoxy,
   j) —$S(O)_x$($C_{1-4}$ alkyl) wherein x is 0, 1 or 2,
   k) —$C_{3-7}$ cycloalkyl;

and the phenyl groups of $R^{2a}$ and $R^{2b}$ may be joined together at the ortho carbon atoms through a carbon-carbon single bond or $C_{1-3}$ alkylene to form a tricyclic group with the $X^2$ to which they are attached;

$X^1$ is —N, —CH or O, and if $X^1$ is O $R^{1a}$ is absent;

$X^2$ is —N or —CH;

$R^3$ is selected from the group consisting of:
1) —$CONR^7R^8$, and
2) —$CO_2R^9$;

$R^4$, $R^5$ and $R^6$ are H or are independently selected from the definitions of $R^3$;

$R^7$ is $C_{1-6}$ alkyl substituted with one or more substituents selected from the group consisting of:
1) —$NHR^{10}$,
2) —$NR^{10}R_{11}$,
3) —NHCO($C_{1-6}$ alkyl),
4) —$NR^{10}CO_2R^{11}$,
5) —N($R^{10}$)(($C_{1-6}$ alkyl)$CONHR^{11}$),
6) —N($CO_2R^{10}$)(($C_{1-6}$ alkyl)$CONHR^{11}$), and
7) —$NR^{10}$($C_{1-6}$alkyl)$CONHR^{11}$;

$R^8$ is H, $C_{1-6}$ alkyl or is independently selected from the definitions of $R^7$;

$R^9$ is H or —$CH_2$-phenyl, wherein the phenyl is either unsubstituted or substituted with one or more substituents selected from the group consisting of:
1) —$C_{1-4}$ alkoxy,
2) -halo,
3) —OH,
4) —$CF_3$
5) —$NH_2$,
6) —NH($C_{1-4}$ alkyl)
7) —N($C_{1-4}$ alkyl)2,
8) —$CO_2H$,
9) —$CO_2$($C_{1-4}$ alkyl), and
10) —$C_{1-6}$ alkyl, either unsubstituted or substituted with one or more substituents selected from the group consisting of:
   a) -halo,
   b) —OH,
   c) —$CF_3$,
   d) —$NH_2$,
   e) —NH($C_{1-4}$ alkyl),
   f) —N($C_{1-4}$ alkyl)($C_{1-4}$ alkyl)
   g) —$CO_2H$,
   h) —$CO_2$($C_{1-4}$ alkyl,
   i) $C_{1-4}$alkoxy,
   j) —$S(O)_x$($C_{1-4}$ alkyl) wherein x is 0, 1 or 2,
   k) —$C_{3-7}$ cycloalkyl;

$R^{10}$ is H, $C_{1-6}$ alkyl, or —($C_{1-6}$ alkyl)-phenyl, wherein the phenyl is either unsubstituted or substituted with one or more substituents selected from the group consisting of:

1) —$C_{1-4}$ alkoxy,
2) -halo,
3) —OH,
4) —$CF_3$,
5) —$NH_2$,
6) —NH($C_{1-4}$ alkyl),
7) —N($C_{1-4}$ alkyl)2,
8) —$CO_2H$,
9) —$CO_2$($C_{1-4}$ alkyl), and
10) —$C_{1-6}$ alkyl, either unsubstituted or substituted with one or more substituents selected from the group consisting of:
 a) -halo,
 b) —OH,
 c) —$CF_3$,
 d) —$NH_2$,
 e) —NH($C_{1-4}$ alkyl),
 f) —N($C_{1-4}$ alkyl)($C_{1-4}$ alkyl)
 g) —$CO_2H$,
 h) —$CO_2$($C_{1-4}$ alkyl),
 i) $C_{1-4}$ alkoxy,
 j) —$S(O)_x$($C_{1-4}$ alkyl) wherein x is 0, 1 or 2,
 k) —$C_{3-7}$ cycloalkyl; and $R^{11}$ is H, $C_{1-6}$ alkyl, or is independently selected from the definitions of $R^{10}$.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, $R^6$, $R^7$, $R^8$, $R^9$, $R^{10}$, $R^{11}$, $R^{12}$, $R^{13}$, etc.) occurs more than one time in any variable or in Formula I, its definition on each ocurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, iso- sec- and tert-butyl, pentyl, hexyl, heptyl, 3-ethylbutyl, and the like. "Alkoxy" represents an alkyl group of indicated number of carbon atoms attached through an oxygen bridge, such as methoxy, ethoxy, propoxy, butoxy and pentoxy. "Alkenyl" is intended to include hydrocarbon chains of a specified number of carbon atoms of either a straight- or branched- configuration and at least one unsaturation, which may occur at any point along the chain, such as ethenyl, propenyl, butenyl, pentenyl, dimethylpentyl, and the like, and includes E and Z forms, where applicable. "Halogen" or "halo", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or pamoate, salicylate and stearate. Similarly pharmaceutically acceptable cations include, but are not limited to sodium, potassium, calcium, aluminum, lithium and ammonium.

The term "aryl" means phenyl or naphthyl either unsubstituted or substituted with one, two or three substituents selected from the group consisting of halo, $C_{1-4}$-alkyl, $C_{1-4}$-alkoxy, $NO_2$, $CF_3$, $C_{1-4}$-alkylthio, OH, —N($R^6$)$_2$, —$CO_2R^6$, $C_{1-4}$-polyfluoroalkyl, $C_{3-6}$polyfluorocycloal and tetrazol-5-yl.

The term "heteroaryl" means an unsubstituted, monosubstituted or disubstituted five or six membered aromatic heterocycle comprising from 1 to 3 heteroatoms selected from the group consisting of O, N and S and wherein the substituents are members selected from the group consisting of —OH, —SH, —$C_{1-4}$-alkyl, —$C_{1-4}$-alkoxy, —$CF_3$, halo, —NO2, —$CO_2R^6$, —N($R^6$)$_2$ and a fused benzo group.

One embodiment of the novel compounds of this invention is that wherein $X^1$ and $X^2$ are both N of structural formula:

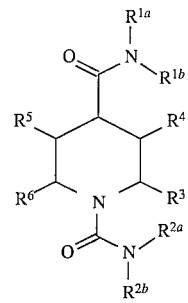

or a pharmaceutically acceptable salt thereof.

A first class of compounds within this embodiment are those compounds wherein:

$R^{1a}$ is selected from the group consisting of:
1) H,
2) $C_{1-8}$ alkyl,
3) phenyl, either unsubstituted or substituted with one or two substituents selected from the group consisting of:
 a) —$C_{1-4}$ alkyl,
 b) -halo,
 c) —OH,
 d) —$CF_3$,
 e) —$NH_2$,
 f) —NH($C_{1-4}$ alkyl),
 g) —N($C_{1-4}$ alkyl)($C_{1-4}$ alkyl),
 h) —$CO_2H$,
 i) —$CO_2$($C_{1-4}$ alkyl), and
 j) —$C_{1-4}$ alkoxy;
4) —$C_{1-4}$alkyl-phenyl, wherein the phenyl is either unsubstituted or substituted with one or two substituents selected from:
 a) —$C_{1-4}$ alkyl,
 b) -halo,
 e) —OH,
 d) —$CF_3$
 e) —$NH_2$,
 f) —NH($C_{1-4}$ alkyl),
 g) —N($C_{1-4}$ alkyl)2,
 h) —$CO_2H$,
 i) —$CO_2$($C_{1-4}$ alkyl), and
 j) —$C_{1-4}$ alkoxy;

$R^{1b}$ is selected from the group consisting of:
1) $R^{1a}$
2) —$C_{3-7}$ cycloalkyl, and
3) —$CH_2$-$R^{1a}$;

$R^{2a}$ and $R^{2b}$ are independently phenyl, either unsubstituted or substituted with one or two substituents selected from the group consisting of:
1) —$C_{1-4}$ alkoxy,
2) -halo,
3) —OH,
4) —$CF_3$,
5) —$NH_2$, 6) —NH($C_{1-4}$ alkyl),
7) —N($C_{1-4}$ alkyl)2,
8) —$CO_2H$,
9) —$CO_2$($C_{1-4}$ alkyl), and
10) —$C_{1-6}$ alkyl, either unsubstituted or substituted with one or more substituents selected from the group consisting of:
   a) -halo,
   b) —OH,
   c) —$CF_3$,
   d) —$NH_2$,
   e) —NH($C_{1-4}$ alkyl),
   f) —N($C_{1-4}$ alkyl)($C_{1-4}$ alkyl)
   g) —$CO_2H$,
   h) —$CO_2$($C_{1-4}$ alkyl),
   i) $C_{1-4}$alkoxy,
   j) —S(O)$_x$($C_{1-4}$ alkyl) wherein x is 0, 1 or 2, and
   k) —$C_{3-7}$ cycloalkyl;
and the phenyl groups of $R^{2a}$ and $R^{2b}$ may be joined together at the ortho carbon atoms through a carbon-carbon single bond or $C_{1-3}$ alkylene to form a tricyclic group with the $X^2$ to which they are attached;

$R^3$ is —$CONR^7R^8$;

$R^4$, $R^5$ and $R^6$ are H;

$R^7$ is $C_{1-6}$ alkyl substituted with one or more substituents selected from the group consisting of:
1) —N($R^{10}$)($CH_2CONHR^{11}$),
2) —N($CO_2R^{10}$)($CH_2CONHR^{11}$), and $R^8$ is H.

Specific compounds within this first class include:
1) trans 1-(N,N-diphenylaminocarbonyl )-2-(RS)-(2-(N(aminocarbonylmeth yl)amino)ethylaminocarbonyl)-4-(RS)-(N,N-dipentylaminocarbonyl)piperidine;
2) trans 1-(N,N-diphenylaminocarbonyl)-2-(RS)-(2-(N-(2methoxybenzyl)-(N-(aminocarbonylmeth yl)amino)ethylaminocarbonyl)-4-(RS)-(N,N-dipentylaminocarbonyl)piperidine;
3) trans 1-(N-(3-chlorophenyl)-N-(phenyl)-aminocarbonyl)-2-(RS)-(2-(N-(benzyloxycarbonyl)-N-(aminocarbonylmethyl)amino)-ethylaminocarbonyl)-4-(RS)-(N,N-dipentylaminocarbonyl)piperidine;
4) trans 1-(N-(3-chlorophenyl)-N-(phenyl)-aminocarbonyl)-2-(RS)(2-N-(aminocarbonylmethyl)amino)ethylaminocarbonyl)-4-(RS)-(N-N-dipentylaminocarbonyl)piperidine;
5) trans 1-(N-(3-chlorophenyl)-N-(phenyl)-aminocarbonyl)-2-(RS)(2-(N-(2-methoxybenzyl)-(N-aminocarbonylmethyl)amino)ethylaminocarbonyl)-4-(RS)-(N,N-dipentylaminocarbonyl)piperidine;
or a pharmaceutically acceptable salt thereof.

A second class of compounds within this embodiment are those compounds wherein:

$R^{1a}$ is selected from the group consisting of:
1) H,
2) $C_{1-8}$ alkyl,
3) phenyl, either unsubstituted or substituted with one or two substituents selected from the group consisting of:
   a) —$C_{1-4}$ alkyl,
   b) -halo,
   c) —OH,
   d) —$CF_3$,
   e) —$NH_2$,
   f) —NH($C_{1-4}$ alkyl),
   g) —N($C_{1-4}$ alkyl)($C_{1-4}$ alkyl),
   h) —$CO_2H$,
   i) —$CO_2$($C_{1-4}$ alkyl), and
   j) —$C_{1-4}$ alkoxy;
4) —$C_{1-4}$alkyl-phenyl, wherein the phenyl is either unsubstituted or substituted with one or two substituents selected from:
   a) —$C_{1-4}$ alkyl,
   b) -halo,
   e) —OH,
   d) —$CF_3$,
   e) —$NH_2$,
   f) —NH($C_{1-4}$ alkyl),
   g) —N($C_{1-4}$ alkyl)$_2$,
   h) —$CO_2H$,
   i) —$CO_2$($C_{1-4}$ alkyl), and
   j) —$C_{1-4}$ alkoxy;

$R^{1b}$ is selected from the group consisting of:
1) $R^{1a}$
2) —$C_{3-7}$ cycloalkyl, and
3) —$CH_2$-$R^{1a}$;

$R^{2a}$ and $R^{2b}$ are independently phenyl, either unsubstituted or substituted with one or two substituents selected from the group consisting of:
1) —$C_{1-4}$ alkoxy,
2) -halo,
3) —OH,
4) —$CF_3$,
5) —$NH_2$,
6) —NH($C_{1-4}$ alkyl),
7) —N($C_{1-4}$ alkyl)$_2$,
8) —$CO_2H$,
9) —$CO_2$($C_{1-4}$ alkyl), and
10) —$C_{1-6}$ alkyl, either unsubstituted or substituted with one or more substituents selected from the group consisting of:
   a) -halo,
   b) —OH,
   c) —$CF_3$,
   d) —$NH_2$,
   e) —NH($C_{1-4}$ alkyl),
   f) —N($C_{1-4}$ alkyl)($C_{1-4}$ alkyl)
   g) —$CO_2H$,
   h) —$CO_2$($C_{1-4}$ alkyl),
   i) $C_{1-4}$alkoxy,
   j) —S(O)$_x$($C_{1-4}$ alkyl) wherein x is 0, 1 or 2,
   k) —$C_{3-7}$ cycloalkyl;
and the phenyl groups of $R^{2a}$ and $R^{2b}$ may be joined together at the ortho carbon atoms through a carbon-carbon single bond or $C_{1-3}$ alkylene to form a tricyclic group with the $X^2$ to which they are attached;

$R^3$ is —$CONR^7R^8$;

$R^4$, $R^5$ and $R^6$ are H;

$R^7$ is $C_{1-6}$ alkyl substituted with —$NR^{10}R^{11}$;

$R^8$ is H;

$R^{10}$ is —($C_{1-6}$alkyl)-phenyl, wherein the phenyl is substituted with —$C_{1-4}$ alkoxy, $R^{11}$ is H, $C_{1-6}$ alkyl, or is independently selected from the definitions of $R^{10}$.

Specific compounds within this second class include:
1) trans 1-(N,N-diphenylaminocarbonyl)-2-(RS)-(2-(N-(2methoxybenzyl)-N-methylamino)ethylaminocarbon-4-(RS)-(N,N-dipentylaminocarbonyl)piperidine;
2) cis 1-(N,N-diphenylaminocarbonyl)-2-(RS)-(2-(N-(2-methoxybenzyl)-N-methylamino)ethylaminocarbonyl (N,N-dipentylaminocarbonyl)piperidine;
3) trans 1-(N-(3-chlorophenyl)—N-(phenyl)-aminocarbonyl)-2-(RS)-(2-(N-(2-methoxybenzyl)-N-methylmino)ethylaminocarbonyl)-4-(RS)-(N,N-dipentylaminocarbonyl)piperdine;

4) trans 1-(N-(3-chlorophenyl)-N-(phenyl)-aminocarbonyl)-2-(RS)-(2-(N-(2-methoxybenzyl)-N-methylamino)ethylaminocarbonyl)-4-(RS)-(N,N-dibenzylaminocarbonyl)piperidine;

or a pharmaceutically acceptable salt thereof.

A third class of compounds within this embodiment are those compounds wherein:

$R^{1a}$ is selected from the group consisting of:
1) H,
2) $C_{1-8}$ alkyl,
3) phenyl, either unsubstituted or substituted with one or two substituents selected from the group consisting of:
   a) —$C_{1-4}$ alkyl,
   b) -halo,
   c) —OH,
   d) —$CF_3$,
   e) —$NH_2$,
   f) —NH($C_{1-4}$ alkyl),
   g) —N($C_{1-4}$ alkyl)($C_{1-4}$ alkyl),
   h) —$CO_2H$,
   i) —$CO_2$($C_{1-4}$ alkyl), and
   j) —$C_{1-4}$ alkoxy;
4) —$C_{1-4}$alkyl-phenyl, wherein the phenyl is either unsubstituted or substituted with one or two substituents selected from:
   a) —$C_{1-4}$ alkyl,
   b) -halo,
   c) —OH,
   d) —$CF_3$
   e) —$NH_2$,
   f) —NH($C_{1-4}$ alkyl),
   g) —N($C_{1-4}$ alkyl)$_2$,
   h) —$CO_2H$,
   i) —$CO_2$($C_{1-4}$ alkyl), and
   j) —$C_{1-4}$ alkoxy;

$R^{1b}$ is selected from the group consisting of:
1) $R^{1a}$
2) —$C_{3-7}$ cycloalkyl, and
3) —$CH_2$-$R^{1a}$;

$R^{2a}$ and $R^{2b}$ are independently phenyl, either unsubstituted or substituted with one or two substituents selected from the group consisting of:
1) —$C_{1-4}$ alkoxy,
2) -halo,
3) —OH,
4) —$CF_3$,
5) —$NH_2$,
6) —NH($C_{1-4}$ alkyl),
7) —N($C_{1-4}$ alkyl)2,
8) —$CO_2H$,
9) —$CO_2$($C_{1-4}$ alkyl), and
10) —$C_{1-6}$ alkyl, either unsubstituted or substituted with one or more substituents selected from the group consisting of:
    a) -halo,
    b) —OH,
    c) —$CF_3$,
    d) —$NH_2$,
    e) —NH($C_{1-4}$ alkyl),
    f) —N($C_{1-4}$ alkyl)($C_{1-4}$ alkyl)
    g) —$CO_2H$,
    h) —$CO_2$($C_{1-4}$ alkyl),
    i) $C_{1-4}$alkoxy,
    j) —$S(O)_x$($C_{1-4}$ alkyl) wherein x is 0, 1 or 2,
    k) —$C_{3-7}$ cycloalkyl; and the phenyl groups of $R^{2a}$ and $R^{2b}$ may be joined together at the ortho carbon atoms through a carbon-carbon single bond or $C_{1-3}$ alkylene to form a tricyclic group with the $X^2$ to which they are attached;

$R^3$ is $CONR^7R^8$;

$R^4$, $R^5$ and $R^6$ are H;

$R^7$ is $C_{1-6}$ alkyl substituted with —$NR^1OR^{11}$;

$R^8$ is H;

$R^{10}$ is $C_{1-6}$ alkyl;

$R^{11}$ is H or $C_{1-6}$ alkyl.

Specific compounds within this third class include:
1) trans 1-(N,N-diphenylaminocarbonyl)-2-(RS)-(3(diethylamino)propylaminocarbonyl) -4-(RS)-(N,N-dipentylaminocarbonyl)piperidine;

or a pharmaceutically acceptable salt thereof.

A fourth class of compounds within this embodiment are those compounds wherein:

$R^{1a}$ is selected from the group consisting of:
1) H,
2) $C_{1-8}$ alkyl,
3) phenyl, either unsubstituted or substituted with one or two substituents selected from the group consisting of:
   a) —$C_{1-4}$ alkyl,
   b) -halo,
   c) —OH,
   d) —$CF_3$,
   e) —$NH_2$,
   f) —NH($C_{1-4}$ alkyl),
   g) —N($C_{1-4}$ alkyl)($C_{1-4}$ alkyl),
   h) —$CO_2H$,
   i) —$CO_2$($C_{1-4}$ alkyl), and
   j) —$C_{1-4}$ alkoxy;
4) —$C_{1-4}$alkyl-phenyl, wherein the phenyl is either unsubstituted or substituted with one or two substituents selected from:
   a) —$C_{1-4}$ alkyl,
   b) -halo,
   e) —OH,
   d) —$CF_3$
   e) —$NH_2$,
   f) —NH($C_{1-4}$ alkyl),
   g) —N($C_{1-4}$ alkyl)$_2$,
   h) —$CO_2H$,
   i) —$CO_2$($C_{1-4}$ alkyl), and
   j) —$C_{1-4}$ alkoxy;

$R^{1b}$ is selected from the group consisting of:
1) $R^{1a}$
2) —$C_{3-7}$ cycloalkyl, and
3) —$CH_2$-$R^{1a}$;

$R^{2a}$ and $R^{2b}$ are independently phenyl, either unsubstituted or substituted with one or two substituents selected from the group consisting of:
1) —$C_{1-4}$ alkoxy,
2) -halo,
3) —OH,
4) —$CF_3$,
5) —$NH_2$,
6) —NH($C_{1-4}$ aklyl,
7) —N($C_{1-4}$ alkyl)2,
8) —$CO_2H$,
9) —$CO_2$($C_{1-4}$ alkyl), and
10) —$C_{1-6}$ alkyl, either unsubstituted or substituted with one or more substituents selected from the group consisting of:
    a) -halo,
    b) —OH, c) —CF$_3$,
d) —NH$_2$,
e) —NH(C$_{1-4}$ alkyl),
f) —N(C$_{1-4}$ alkyl)(C$_{1-4}$ aklyl)
g) —CO$_2$H,
h) —CO$_2$(C$_{1-4}$ alkyl),
i) C$_{1-4}$alkoxy,
j) —S(O)$_x$(C$_{1-4}$ alkyl) wherein x is 0, 1 or 2,
k) —C$_{3-7}$ cycloalkyl;

and the phenyl groups of R$^{2a}$ and R$^{2b}$ may be joined together at the ortho carbon atoms through a carbon-carbon single bond or C$_{1-3}$ alkylene to form a tricyclic group with the X$^2$ to which they are attached;

R$^3$ is —CO$_2$R$^9$;

R$^4$, R$^5$ and R$^6$ are H;

R$^9$ is H.

Specific compounds within this fourth class include:
1) trans 1 -(N,N-diphenylaminocarbonyl)-4-(RS)-(N,N-dipentylaminocarbonyl)piperidine-2-(RS)-carboxylic acid;
2) trans 1-(N-(3-chlorophenyl)-N-(phenyl)-aminocarbonyl)-4-(RS) (N,N-dipentylaminocarbonyl)piperidine-2-(RS)-carboxylic acid;

or a pharmaceutically acceptable salt thereof.

Especially preferred compounds include those of structural formula II:

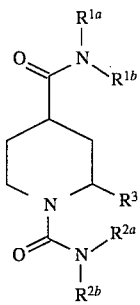

II or a pharmaceutically acceptable salt thereof, wherein:

R$^{1a}$ is selected from the group consisting of:
1) C$_{5-6}$ alkyl,
2) phenyl,
3) —CH$_2$-phenyl, R$^{1b}$ is selected from the definitions of R$^{1a}$;

R$^{2a}$ and R$^{2b}$ are independently phenyl, either unsubstituted or substituted with one substituent selected from the group consisting of:
1) —OCH$_3$,
2) —Cl,
3) —CF$_3$,
4) —CH$_3$;

R$^3$ is selected from the group consisting of:
1) —CONR$^7$R$^8$, and
2) —CO$_2$R$^9$;

R$^7$ is C$_{1-6}$alkyl substituted with one or more substituents selected from the group consisting of:
—NHR$^{10}$,
2) —NR$^{10}$R$^{11}$,
3) —NHCO (C$_{1-6}$ alkyl),
4) —NR$^{10}$CO$_2$R$^{11}$,
—N(CO$_2$R$^{10}$)((C$_{1-6}$alkyl)CONHR$^{11}$),
5) —N(CO$_2$R$^{10}$)((C$^{1-6}$ alkyl)CONHR$^{11}$),
6) NR$^{10}$(C$_{1-6}$alkyl)CONHR$^{11}$;

R$^8$ is H, C$_{1-6}$ alkyl or is independently selected from the definitions of R$^7$;

R$^9$ is H or —CH$_2$-phenyl, wherein the phenyl is either unsubstituted or substituted with one or more substituents selected from the group consisting of:

1) —C$_{1-4}$ alkoxy,
2) -halo,
3) —OH,
4) —CF$_3$
5) —NH$_2$,
6) —NH(C$_{1-4}$ alkyl),
7) —N(C$_{1-4}$ alkyl)$_2$,
8) —CO$_2$H,
9) —CO$_2$(C$_{1-4}$ alkyl), and
10) —C$_{1-6}$ alkyl, either unsubstituted or substituted with one or more substituents selected from the group consisting of:
  a) -halo,
  b) —OH,
  c) —CF$_3$,
  d) —NH$_2$,
  e) —NH(C$_{1-4}$ alkyl),
  f) —N(C$_{1-4}$ alkyl)(C$_{1-4}$ alkyl)
  g) —CO$_2$H,
  h) —CO$_2$(C$_{1-4}$ alkyl),
  i) C$_{1-4}$alkoxy,
  j) —S(O)$_x$(C$_{1-4}$ alkyl) wherein x is 0, 1 or 2,
  k) —C$_{3-7}$ cycloalkyl;

R$^{10}$ is —(C$_{1-4}$ alkyl)-phenyl, wherein the phenyl is either unsubstituted or substituted with one or more substituents selected from the group consisting of:
1) —OCH3,
2) —Cl,
3) —CF$_3$,
4) —CH$_3$; and R$^{11}$ is H, C$_{1-6}$ alkyl, or is independently selected from the definitions of R$^{10}$.

The useful activities of the compounds of this invention are demonstrated and exemplified by the following assays.

TACHYKININ ANTAGONISM ASSAY

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assay.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM CaCl$_2$, 1.2 mM MgCl$_2$, 2.4 mM K$_2$HPO$_4$, 0.6 mM KH$_2$PO$_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100U/ml penicillinstreptomycin, and 90% DMEM media (GIBCO, Grand Island, N.Y.) in 5% CO$_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer supplemented with 0.625 mg/ml Herring sperm DNA at 300 V and 950 uF using the IBI GENEZAPPER (IBI). The transfected cells were incubated in CHO media [10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)]in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 11 of unlabeled substance p or any other test compound. The tubes were incubated at 4° C. or at room temperature for 1 hour with gentle shaking. The bound radioactivity was separated from unbound radioactivity by GF/C filter (BRANDEL, Gaithersburg, M.d.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1N HCl is added. Each well is sonicated at 4° C. and extracted with $CHCl_3$/methanol (1:1). The aqueous phase is applied to a 1 ml Dowex AG 1X8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

The compounds of the present invention are useful in the prevention and treatment of a wide variety of clinical conditions which are characterized by the presence of an excess of tachykinin, in particular substance P, activity.

These conditions may include disorders of the central nervous system such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic neuropathy, chemotherapy-induced neuropathy, and postherpetic and other neuralgias; respiratory diseases such as chronic obstructive airways disease, bronchopneumonia, chronic bronchitis, bronchospasm and asthma; airways disease modulated by neurogenic inflammation; diseases characterized by neurogenic mucus secretion, such as cystic fibrosis; diseases associated with decreased glandular secretions, including lacrimation, such as Sjogren's syndrome, hyperlipoproteinemias IV and V, hemochromatosis, sarcoidosis, or amyloidosis; inflammatory diseases such as inflammatory bowel disease, irritable bowel syndrome, psoriasis, fibrositis, ocular intimation, osteoarthritis and rheumatoid arthritis; allergies such as eczema and rhinitis; hypersensitivity disorders such as poison ivy; ophthalmic diseases such as conjunctivitis, vemal conjunctivitis, dry eye syndrome, and the like; cutaneous diseases such as contact dermatitis, atropic dermatitis, urticaria, and other eczematoid dermatitis; oedema, such as oedema caused by thermal injury; addiction disorders such as alcholism; stress related somatic disorders; reflex sympathetic dystrophy such as shoulder/hand syndrome; dysthymic disorders; adverse immunological reactions such as rejection of transplanted tissues and disorders related to immune enhancement or suppression, such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed, post-operative, late-phase, and anticipatory emesis, for example, induced by chemotherapy, radiation, toxins, pregnancy, vestibular disorder, motion, post-opearative sickness, surgery, gastrointestinal obstruction, reduced gastrointestinal motility, visceral pain, migraine, opioid analgesics and variations in intercranial pressure (except quaternary salts); disorders of bladder function such as bladder detrusor hyperreflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, chronic pain or that attributable to or associated with any of the foregoing conditions especially the transmission of pain in migraine. Hence, these compounds may be readily adapted to therapeutic use for the treatment of physiological disorders associated with an excessive stimulation of tachykinin receptors, especially neurokinin-1, and as neurokinin-1 antagonists in the control and/or treatment of any of the aforesaid clinical conditions in mammals, including humans.

For example, the compounds of the present invention may suitably be used in the prevention or treatment of disorders of the central nervous system such as anxiety, psychosis and schizophrenia; neurodegenerative disorders such as senile dementia of the Alzheimer type, Alzheimer's disease and Down's syndrome; respiratory diseases, particularly those associated with excess mucus secretion, such as chronic obstructive airways disease, broncho-pneumonia, chronic bronchitis, cystic fibrosis and asthma, and bronchospasm; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine (both prophylaxis and acute treatment).

As calcium channel blocking agents some of the compounds of the present invention are useful in the prevention of treatment of clinical conditions which benefit from inhibition of the transfer of calcium ions across the plasma membrane of cells. These include diseases and disorders of the heart and vascular system such as angina pectoris, myocardial infarction, cardiac arrhythmia, cardiac hypertrophy, cardiac vasospasm, hypertension, cerebrovascular spasm and other ischemic disease. Furthermore, these compounds may be capable of lowering elevated intraocular pressure when administered topically to the hypertensive eye in solution in a suitable ophthalmic vehicle. Also, these compounds may be useful in the reversal of multidrag resistance in rumor cells by enhancing the efficacy of chemotherapeutic agents. In addition, these compounds may have activity in blocking calcium channels in insect brain membranes and so may be useful as insecticides.

The compounds of the present invention are particularly useful in the treatment of pain or nociception and/or inflammation and disorders associated therewith such as, for example: neuropathy, such as diabetic or peripheral neuropathy and chemotherapy-induced nemopathy; postherpetic and other neuralgias; asthma; osteoarthritis; rheumatoid arthritis; and especially migraine. The compounds of the present invention are also particularly useful in the treatment of diseases characterized by neurogenic mucus secretion, especially cystic fibrosis.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carder or excipient suitable for external, enteral or parenteral applications. The active ingredient may be compounded, for example, with the usual non-toxic, pharmaceutically acceptable carders for tablets, pellets, capsules, suppositories, solutions, emulsions, suspensions, and any other form suitable for use. The carders which can be used are water, glucose, lactose, gum acacia, gelatin, mannitol, starch paste, magnesium trisilicate, talc, corn starch, keratin, colloidal silica, potato starch, urea and other carders suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carder, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques.

For the treatment of certain conditions it may be desirable to employ a compound of the present invention in conjunction with another pharmacologically active agent. For example, for the treatment of respiratory diseases such as asthma, a compound of the present invention may be used in conjunction with a bronchodilator, such as a $\beta_2$-adrenergic receptor agonist or tachykinin antagonist which acts at neurokinin-2 receptors. Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis, a compound of the present invention may be used in conjunction with a tachykinin antagonist which acts at neurokinin-2 receptors, or with tachykinin receptor antagonist which acts at both neurokinin-1 and neurokinin-2 receptors. Similarly, for the prevention or treatment of emesis a compound of the present invention may be used in conjunction with other anti-emetic agents, especially 5HT$_3$ receptor antagonists, such as ondansetron, granisetron, tropisetron, decadron, and zatisetron. Likewise, for the prevention or treatment of migraine a compound of the present invention may be used in conjunction with other anti-migraine agents, such as ergotamines or 5HT$_1$ agonists, especially sumatriptan. For the prevention or treatment of inflammatory conditions in the lower urinary tract, especially cysfitis, a compound of the present invention may be used in conjunction with an antiinflammatory, such as a bradykinin receptor antagonist. The compound of the present invention and the other pharmacologically active agent may be administered to a patient simultaneously, sequentially or in combination.

The compounds of this invention may be administered to patients (animals and human) in need of such treatment in dosages that will provide optimal pharmaceutical efficacy. The dose will vary from patient to patient depending upon the nature and severity of disease, the patient's weight, special diets then being followed by a patient, concurrent medication, and other factors which those skilled in the art will recognize.

In the treatment of a condition associated with an excess of tachykinins, an appropriate dosage level will generally be about 0.001 to 50 mg per kg patient body weight per day which can be administered in single or multiple doses. Preferably, the dosage level will be about 0.005 to about 25 mg/kg per day; more preferably about 0.01 to about 10 mg/kg per day; and even more preferably about 0.05 to about 1 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.01 to 5 mg/kg per day. The compounds may be administered on a regimen of 1 to 4 times per day, preferably once or twice per day.

Several methods for preparing the compounds of this invention are illustrated in the following Schemes and Examples wherein $R^1$, $R^2$, $R^3$, $R^4$, $R^5$, $R^6$, $R^7$, $R^8$, $R^9$, $R^{10}$ and $R^{11}$ are as defined above.

TABLE 1

ABBREVIATIONS USED IN SCHEMES AND EXAMPLES

Reagents:

| | |
|---|---|
| Et$_3$N | triethylamine |
| Ph$_3$P | triphenylphosphine |
| TFA | trifluoroacetic acid |
| NaOEt | sodium ethoxide |
| DCC | N,N'-dicyclohexylcarbodiimide |
| DCU | N,N'-dicyclohexylurea |
| CDI | 1,1'-carbonyldiimidazole |
| MCPBA | m-chloroperbenzoic acid |
| DBU | 1,8-diazabicyclo[5.4.0]undec-7-ene |
| Cbz-Cl | benzyl chloroformate |
| ACE-Cl | alpha-chloroethyl chloroformate |
| iPr$_2$NEt or DIEA | N,N-diisopropylethylamine |
| NHS | N-hydroxysuccinimide |
| DIBAL | diisobutylaluminum hydride |
| Me$_2$SO$_4$ | dimethyl sulfate |
| HOBt | 1-hydroxybenzotriazole hydrate |

TABLE 1-continued

ABBREVIATIONS USED IN SCHEMES AND EXAMPLES

| | |
|---|---|
| EDAC | 1-ethyl-3-(3-dimethylaminopropyl)carbodiimide hydrochloride |

Solvents:

| | |
|---|---|
| DMF | dimethylformamide |
| THF | tetrahydrofuran |
| MeOH | methanol |
| EtOH | ethanol |
| AmOH | n-amyl alcohol |
| AcOH | acetic acid |
| MeCN | acetonitrile |
| DMSO | dimethylsulfoxide |

Others:

| | |
|---|---|
| Ph | phenyl |
| Ar | aryl |
| Me | methyl |
| Et | ethyl |
| iPr | isopropyl |
| Am | n-amyl |
| Cbz | carbobenzyloxy (benzyloxy-carbonyl) |
| BOC | tert-butoxycarbonyl |
| PTC | phase transfer catalyst |
| cat. | catalytic |
| FAB-MS | fast atom bombardment mass spectrometry |
| rt | room temperature |

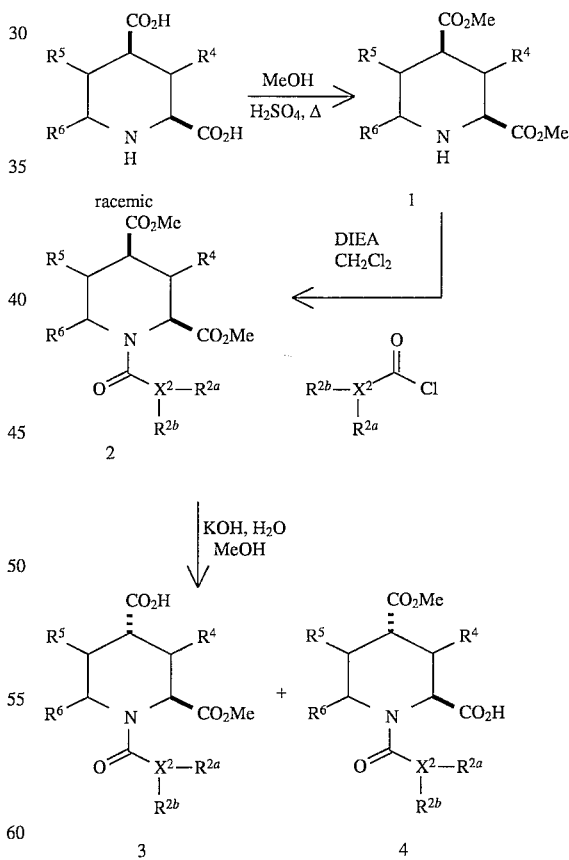

SCHEME 1

5,610,165
21
SCHEME 2
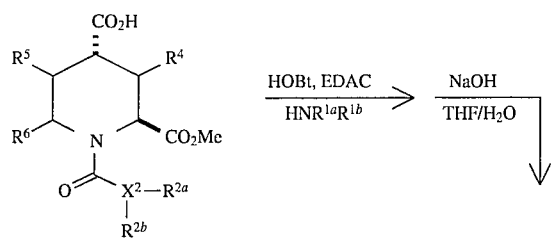
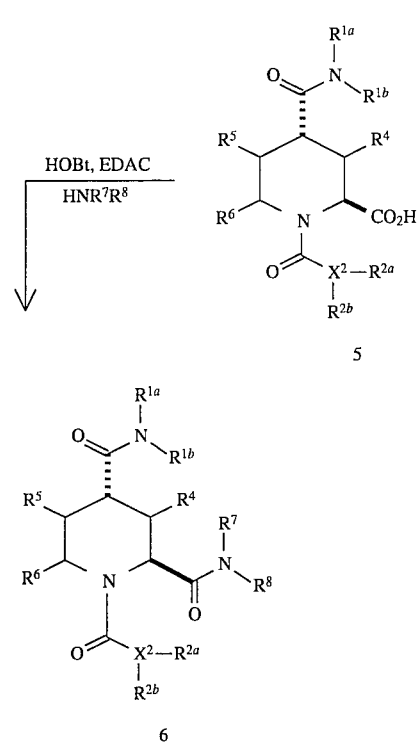
SCHEME 3
22
-continued
SCHEME 3
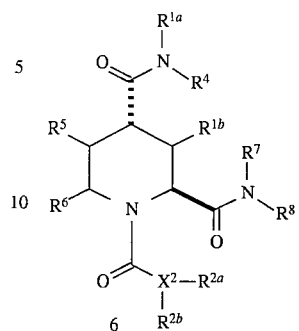
SCHEME 4
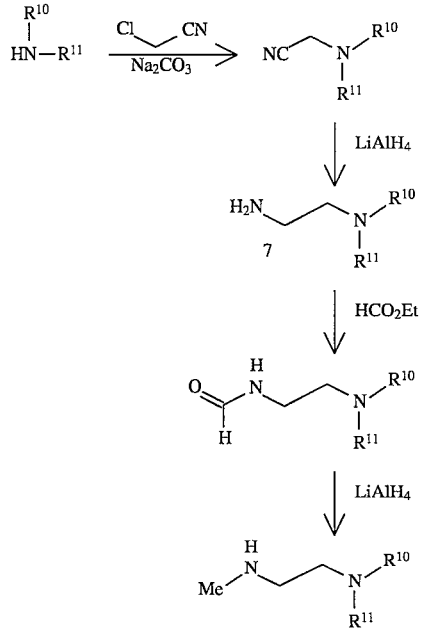
SCHEME 5
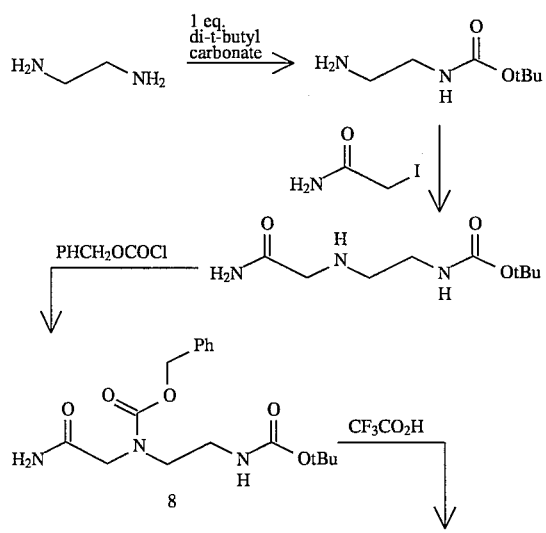

23

-continued
SCHEME 5

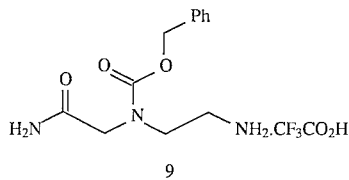
9

SCHEME 6

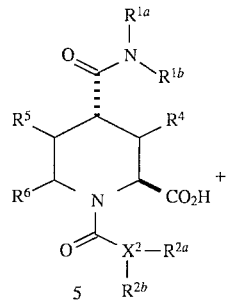
5

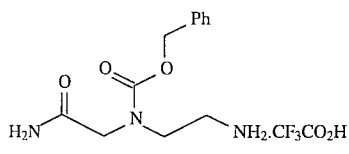
9

↓ DIEA, EDAC
HOBt

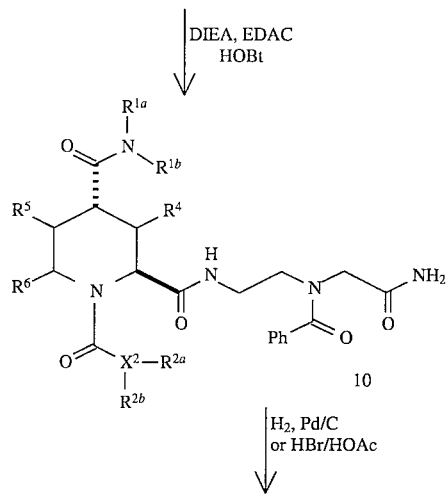
10

↓ H₂, Pd/C
or HBr/HOAc

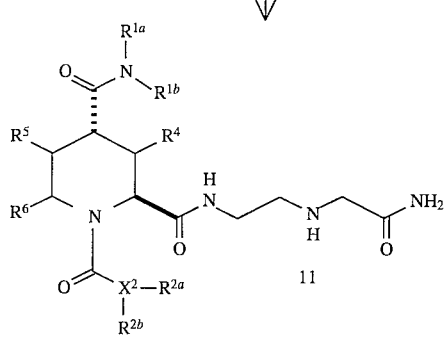
11

24

-continued
SCHEME 6

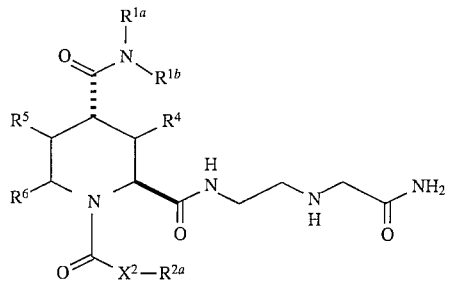
11

↓ Cl–CH₂–Ar
DIEA

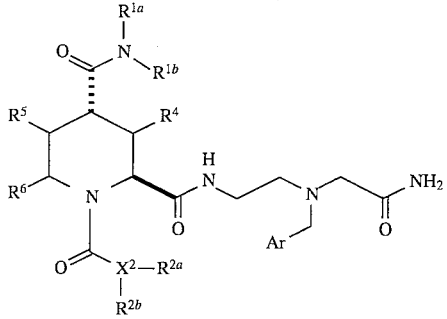
12

The compounds of the present invention in which $X^2$=N can be prepared according to the procedure given in Scheme 1. Esterification of the commercially available cis-piperidine-2,4dicarboxylic acid under acidic conditions yields the diester 1. Acylation on nitrogen with, for example, N,N-diphenylcarbamyl chloride ($R^{1a}$=$R^{1b}$=Ph) provides the urea 2. Exposure of the diester 2 to one equivalent of aqueous base followed by acidification produces a mixture of the 4-carboxylic acid 3 and the 2-carboxylic acid 4, along with lesser quantities of the diacid. During the base hydrolysis step, epimerization to the more stable trans 2,4-disubstituted piperidine takes place. The extent of epimerization is dependent in part on the composition of the solvent: the lower the concentration of water present, the greater the degree of epimerization. If product enriched in cis-isomer is desired, the hydrolysis can be run in water with a minimum of organic solvent present, and the reaction should be stopped before completion.

The products 3 and 4 can be separated and carried on separately as shown in Schemes 2 and 3. In each case, the free acid is converted to the corresponding amide under standard conditions, the remaining ester is hydrolysed, for example to give 5, and the revealed acid is functionalized to provide the product 6.

The side chains of interest can be prepared by several routes. For example, the ethylenediamine derivatives can be synthesized according to Scheme 4 if $R^{10}$ and $R^{11}$ do not contain groups susceptible to reduction with lithium aluminum hydride. If the N-methyl amide is not desired, the primary amine 7 can be used directly in the coupling reaction with the piperidine substrates.

For preparation of the N-methylcarboxamide containing sidechains, the chemistry shown in Scheme 5 can be employed. Monoprotection with an acylating agent such as di-t-butyl carbonate followed by alkylation of the remaining basic nitrogen with iodoacetamide is followed by orthogonal protection, for example by CBZ chloride, to give the doubly protected intermediate 8. This compound can then be selectively deprotected to yield the desired side chain 9.

After coupling 9 to 5 with a suitable condensing agent, for example, EDAC in the presence of HOBt in methylene chloride with a base present such as DIEA to free 9 from its salt, the product 10 can be deprotected under hydrogenolytic conditions to give the tetra-amide 11. Alternatively, if groups incompatible with reducing conditions are present, HBr in acetic acid can be employed to cleave the CBZ protecting group. The amine 11 can be optionally alkylated, for example with a benzyl chloride derivative, to provide the product 12.

The object compounds of Formula I obtained according to the reactions as explained above can be isolated and purified in a conventional manner, for example, extraction, precipitation, fractional crystallization, recrystallization, chromatography, and the like.

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Although the reaction schemes described herein are reasonably general, it will be understood by those skilled in the art of organic synthesis that one or more functional groups present in a given compound of formula I may render the molecule incompatible with a particular synthetic sequence. In such a case an alterative route, an altered order of steps, or a strategy of protection and deprotection may be employed. In all cases the particular reaction conditions, including reagents, solvent, temperature, and time, should be chosen so that they are consistent with the nature of the functionality present in the molecule.

The following examples are given for the purpose of illustrating the present invention and shall not be construed as being limitations on the scope or spirit of the invention.

EXAMPLE 1

Trans 1-(N,N-diphenylaminocarbonyl)-2-(RS)-(3-(diethylamino)propylaminocarbonyl)-4-(RS)-(N,N-dipentylaminocarbonyl)piperidine Step A:

Cis dimethyl piperidine-2-(RS),4-(SR)-dicarboxylate

To a suspension of 0.36 g (2.08 mmole) of cis piperidine-2(RS),4-(SR)-dicarboxylate in 20 mL of dry methanol was added 0.4 g (4.2 mmole) of concentrated sulfuric acid, and the mixture was heated at reflux under a drying tube for 72 hr. The cooled solution was treated with solid sodium carbonate and water and was stirred for 2 hr, after which the bulk of the volatiles were removed in vacuo. The residue was purified by flash chromatography on 34 g of silica eluting with 700 mL of 2:100:0.1 methanol:methylene chloride: concentrated aqueous ammonia to give 342 mg (82%) of an oil.

NMR (CDCl$_3$, 400 MHz, ppm): δ 1.45–1.60 (m, 2H), 1.83 (br s, 1H), 1.88 (dm, 1H), 2.27 (dm, 1H), 2.42 (dt, 1H), 2.63 (td, 1H), 3.20 (dm, 1H), 3.31 (dd, 1H), 3.66 (s, 3H), 3.70 (s, 3H).

Step B:

Cis dimethyl 1-(N,N-diphenylaminocarbonyl)piperidine-2-(RS),4-(SR)-dicarboxylate A solution of 0.34 g (1.69 mmole) of cis dimethyl piperidine-2-(RS),4-(SR)-dicarboxylate (from Example 1, Step A above), 0.431 g (1.86 mmole) of diphenylcarbamyl chloride, and 0.234 mL (1.86 mmole) of triethylamine in 6 mL of methylene chloride was stirred under nitrogen at room temperature for 48 hr and then at reflux for 60 hr. After cooling to room temperature, the mixture was purified by flash chromatography on 65 g of silica eluting with 1.5 L of 66:33 hexanes:ethyl acetate to provide 567 mg (85%) of an oily solid. NMR (CDCl$_3$, 400 MHz, ppm):δ 1.45–1.65 (m, 2H), 2.0–2.1 (m, 1H), 2.18–2.27 (m, 1H), 2.53 (pentet, 1H), 3.25–3.35 (m, 1H), 3.4–3.5 (m, 1H), 3.62 (s, 3H), 3.72 (s, 3H), 4.39 (t, 1H), 7.18–7.25 (m, 6H), 7.25–7.33 (m, 4H).

Step C:

Trans methyl 1-(N,N-diphenylaminocarbonyl)piperidine-2-(RS) -carboxylic acid-4-(RS)-carboxylate and trans methyl-1-(N,N-diphenylaminocarbonyl)piperidine-4-(RS)-carboxylic acid-2-(RS)-carboxylate A solution of 63 mg (0.16 mmole) of cis dimethyl 1-(N,N-diphenylaminocarbonyl)piperidine-2-(RS),4-(SR)-dicarboxylate (from Example 1, Step B above) in 1 mL of methanol was treated with a solution of 10 mg (0.16 mmole) of potassium hydroxide in 0.5 mL of methanol at -10 deg C. The mixture was allowed to warm to room temperature and was stirred for 18 hr, at which time 1 drop of water was added. After stirring an additional 24 hr, 2 more drops of water were added. After an additional 48 hr, the mixture was treated with 2 drops of 2N aqueous hydrochloric acid and the volatiles were removed with a stream of nitrogen. The residue was purified by flash chromatography on 16 g silica eluting with 500 mL of 1.8:100:0.12 methanol:methylene chloride:acetic acid to give 34 mg of high Rf product (A) and 20 mg of low Rf product (B) (total yield 88%). By analysis of mass spectral fragmentation patterns and NMR data for reaction products, A was assigned as trans methyl 1-(N,N-diphenylaminocarbonyl)piperidine -4-(RS)-carboxylic acid-2(RS)-carboxylate and B was assigned as trans methyl 1-(N,N-diphenylaminocarbonyl)-piperidine-2-(RS)-carboxylic acid-4-(RS)-carboxylate.

Mass Spectrum (FAB): For compound A—m/Z 383 (M+H, 100%), 337 (M—$CO_{2, 3}$%), 323 (M—$CO_2$Me, 13%), 196 (100%), 186(70%), 168 (35%), 154 (25%), 136 (18%);

For compound B—m/Z 383 (M+H, 100%), 337 (M—$CO_2$, 20%), 323 (M—$CO_2$Me, negligible), 196 (90%), 154 (85%), 136 (80%), 123 (25%).

NMR ($CDCl_3$, 400 MHz, ppm): For compound A: δ 1.33 (qd, 1H; $H_{5ax}$), 1.5–1.7 (br m, 1H; $H_{3ax}$), 1.78 (d, 1H; $H_5$eq), 2.3–2.4 (m, 2H; $H_{3eq}$, $H_{4ax}$), 2.93 (td, 1H; $H_{6ax}$), 3.75 (s, 3H; $CH_3$), 3.88 (d, 1H; $H_{6eq}$), 4.99 (d, 1H; $H_{2eq}$), 7.05–7.15 (m, 6H; aromatic), 7.25–7.33 (m, 4H; aromatic).

For compound B: δ 1.03 (qd, J=13, 4, 1H; $H_{5ax}$), 1.57–1.69 (m, 2H; $H_{3ax}$, $H_{5eq}$), 2.41 (d, J=12.2, 1H; $H_{3eq}$), 2.63 (tt, J=12.4, 3.7, 1H; $H_{4ax}$), 2.93 (td, J=13.3, 2.2, 1H; $H_{6ax}$), 3.63 (s, 3H; $CH_3$), 3.71 (br d, J=12.4, 1H; $H_{6eq}$), 4.83 (d, J=4.8, 1H; $H_{2eq}$), 7.05–7.35 (m, 10H, aromatic).

Step D:

Trans methyl 1-(N,N-diphenylaminocarbonyl)-4-(RS)-(N,N-dipentylaminocarbonyl)piperidine-2-(RS)-carboxylate A solution of 0.034 g (0.089 mmole) of trans methyl 1-(N,N-diphenylaminocarbonyl)piperidine-4-(RS)-carboxylic acid-2- (RS)-carboxylate (from Example 1, Step C above) and 0.013 mg (0.098 mmole) of HOBt at 0 deg C. under nitrogen was treated with 0.024 g (0.12 mmole) of EDAC. The bath was removed after 2 min, and after 35 min more, 0.028 g (0.18 mmole) of di-n-pentylamine was added, and the reaction mixture was stirred for 20 hr. The reaction mixture was purified by flash chromatography on 16 g of silica eluting with 500 mL of 75:25 hexanes: ethyl acetate and then 200 mL of 50:50 hexanes:ethyl acetate to give 22 mg (48%) of an oil; a small amount of the cis isomer was also isolated.

Mass Spectrum (FAB): m/Z523 (M+H, 15%), 463 (M—$CO_2$Me+H, 25%), 325 (M—Ph2NCO, 100%), 196 (Ph2NCO, 65%), 168, $Ph_2$N, 38%), 140 (60%).

NMR ($CDCl_3$, 400 MHz, ppm): δ0.88 (q, 6H), 1.15–1.35 (m, 8H), 1.35–1.75 (m, 6H), 2.09 (d, 1H), 2.49 (tt, 1H), 2.86 (td, 1H), 3.1–3.3 (m, 4H), 3.76 (s, 3H), 3.90 (d, 1H), 4.99 (br s, 1H), 7.05–7.15 (m, 6H), 7.27–7.33 (m, 4H).

Step E:

Trans 1-(N,N-diphenylaminocarbonyl)-4-(RS)-(N,N-dipentylaminocarbonyl)piperidine-2-(RS)-carboxylic acid To a suspension of 0.022 g (0.042 mmole) of trans methyl 1 -(N,N-diphenylaminocarbonyl )-4-(RS)-(N,N-dipentylaminocarbonyl) piperidine-2-(RS)-carboxylate (from Example 1, Step D above) in 0.75 mL of THF and 0.50 mL (0.042 mmole) of water was added 0.017 mL of 2.5N aqueous sodium hydroxide, and the mixture was stirred at room temperature for 50 hr, at which time 0.005 mL (0.0014 mmole) more 2.5N aqueous sodium hydroxide solution was added. After an additional 24 hr, the mixture was treated with 1 drop of 2N aqueous hydrochloric acid and the volatiles were removed in a stream of nitrogen. The residue was purified by flash chromatography on 16 g of silica eluting with 400 mL of 3:100:0.1 methanol:methylene chloride:acetic acid to give 21 mg (100%) of an oil.

Mass Spectrum (FAB): m/Z 508 (M+H, 40%), 462 (M—$CO_2$H, 15%), 343 (15%), 266 (40%), 196 (100%).

NMR ($CDCl_3$, 400 MHz, ppm): δ0.86 (2 to, 6H), 1.15–1.35 (m, 10H), 1.45 (pentet, 3H), 1.4–1.5 (m, 1H), 1.73 (td, 1H), 2.15 (br d, 1H), 2.88 (td, 2H), 3.08–3.20 (2H), 3.3–3.5 (m, 2H), 3.72 (br d, 1H), 4.78 (d, 1H) 7.10 (d, 4H), 7.17 (t, 2H), 7.34 (t, 4H).

Step F:

Trans 1-(N,N-diphenylaminocarbonyl)-2-(RS)-(3-(diethylamino)propylaminocarbonyl)-4-(RS)-(N,N-dipentylaminocarbonyl)piperidine A solution of 0.022 g (0,043 mmole) of trans 1-(N,N-diphenylaminocarbonyl)-4-(RS)-(N,N-dipentylaminocarbonyl)-piperidine-2-(RS)-carboxylic acid (from Example 1, Step E above) and 0.007 g (0.052 mmole) of HOBt in 1 mL of dry methylene chloride was cooled to 0 deg C. under nitrogen and was treated with 0,013 g (0.052 mmole) of EDAC. The cooling bath was removed and after 55 min total the mixture was treated with 0,012 mL (0,087 mmole) of N,N-diethylethylenediamine, and the mixture was stirred at room temp for 22 hr. The mixture was purified by flash chromatography on 16 g of silica eluting with 7:100:0.2 methanol:methylene chloride: concentrated aqueous ammonia to give 28 mg (~100%) of an oil.

Mass Spectrum (FAB): m/Z 620 (M+H, 100%), 463 (M—$CONH(CH_2)_3NEt_2$, 20%), 293 (15%), 196 (55%), 168 (25%), 112 (20%).

NMR ($CDCl_3$, 400 MHz, ppm): a 0.85 (2 to, 6H), 1.04 (t, 6H), 1.1–1.35 (m, 11H), 1.43 (pentet, 2H), 1.5–1.75 (m, 5H), 2.15 (br d, 1H), 2.4–2.7 (br m, 6H), 2.86 (td, 1H), 2.9–3.2 (m, 3H), 3.2–3.45 (m, 3H), 3.45–3.55 (m, 1H), 3.76 (br d, 1H), 4.76 (d, 1H), 7.07 (d, 4H), 7.15 (t, 2H), 7.33 (t, 4H).

EXAMPLE 2

Trans 1-(N,N-diphenylaminocarbonyl)-2-(RS)-(2-(N-(2-methoxybenzybenzyl) -N-methylamino)ethylaminocarbonyl)-4-(RS)-(N,N-dipentylaminocabonyl))piperidine.

Step A:

Racemic cis and trans methyl 1-(N,N-diphenylaminocarbonyl)piperidine-2-carboxylic acid-4-carboxylate and racemic cis and trans methyl 1-(N,N-diphenylaminocarbonyl)piperidine-4-carboxylic acid-2-carboxylate A solution of 0.478 g (1.21 mmole) of cis dimethyl 1(N,N-diphenylaminocarbonyl)piperidine-2-(RS), 4-(SR)-dicarboxylate (from Example 1, Step B above) in 6 mL of methanol was treated with 0.08 g (1.21 mmole) of potassium hydroxide in 2 mL of a 1:1 mixture of methanol:water at room temperature, and the mixture was stirred for 22 hr. The solution was then treated with 2N aqueous hydrochloric acid until the pH was 4, and the mixture was concentrated in vacuo. The residue was purified by flash chromatography on 130 g of silica eluting with 3 L of 2.2:100:0.13 methanol: methylene chloride:concentrated aqueous ammonia to give 322 mg of high Rf material, which by proton NMR analysis was a 2:1 mixture of cis:trans methyl 1-(N,N-diphenylaminocarbonyl)piperidine-4-carboxylic acid-2-carboxylate and 62 mg of low Rf material, which by proton NMR was a 1:2.75 ratio of cis:trans methyl 1-(N,N-diphenylaminocarbonyl)piperidine-2-carboxylic acid-4-carboxylate (total yield 83%). Separation of cis and trans isomers could be achieved after further derivatization.
Step B:

Preparation of
N-(2-Methoxybenzyl)—N-methylethylenediamine a) N-(2-Methoxybenzyl)—N-(methyl)aminoacetonitrile A mixture of 2.0 g (13.2 mmole) of N-methyl-2methoxybenzylamine, 0.99 g (13.2 mmole) of chloroacetonitrile, and 2.80 g (26.5 mmole) of powdered sodium carbonate was stirred in 30 mL of acetone at room temperature for 4 days. The mixture was concentrated in vacuo and the residue purified by flash chromatography on 130 g of silica gel eluting with 83:17 hexanes: ethyl acetate to give 2.2g (87%) of an oil.

$^1$H NMR (CDCl$_3$, 400 MHz, ppm): δ 2.43 (s, 3H), 3.48 (s, 2H), 3.62 (s, 2H), 3.83 (s, 3H), 6.88 (d, 1H), 6.93 (t, 1H), 7.2–7.3 (m, 2H).

b) N-(2-Methoxybenzyl)—N-methylethylenediamine

To a stirred slurry of 0.56 g (15 mmole) of lithium aluminum hydride in 15 mL of diethyl ether under an atmosphere of nitrogen was added a solution of 2.2 g (11.6 mmole) of N-(2-Methoxybenzyl)-N-(methyl)-aminoacetonitrile in 20 mL of diethyl ether. The mixture was heated at reflux for 1 hour and then was allowed to cool to room temperature. The excess hydride was quenched cautiously with aqueous sodium hydroxide, and the resulting suspension was filtered through a pad of sodium sulfate, which was rinsed with additional diethyl ether. The flitrate was concentrated in vacuo to give 2.25 g (~100%) of a clear oil.

$^1$H NMR (CDCl$_3$, 200 MHz, ppm): δ 1.30 (br s, 2H), 2.20 (s, 3H), 2.46 (t, 2H), 2.80 (t, 2H), 3.49 (s, 2H), 3.79 (s, 3H), 6.8–6.95 (m, 2H), 7.15–7.35 (m, 2H).
Step C:

Trans methyl 1-(N,N-diphenylaminocarbonyl)-2-(RS)-(2(N-(2-methoxybenzyl)-N-methylamino)ethylamino-carbonyl)piperidine-4-(RS)-carboxylate A solution of 0.060 g (0.16 mmole) of a 1:2.75 cis:trans racemic mixture of methyl 1-(N,N-diphenylaminocarbonyl)piperidines 2-carboxylic acid-4-carboxylate (from Example 2, Step A above) and 0.023 g (0.17 mmole) of HOBt in 2 mL of dry methylene chloride was cooled to 0 deg C. under nitrogen and was treated with 0.042 g (0.22 mmole) of EDAC. The cooling bath was removed and after 40 min total 0.061 g (0.31 mmole) of N-(2-methoxybenxyl)-N-methylethyl-enediamine (from Example 2, Step B above) was added and the mixture was stirred at room temperature for 24 hr. The mixture was purified by flash chromatography on 16 g of silica eluting with 400 mL of 4:100 methanol: methylene chloride and then 300 mL of 6:100:0.25 methanol:methylene chloride:concentrated aqueous ammonia to give 56 mg (64% yield uncorrected for purity of the starting material) of the trans product as an oil.

Mass Spectrum (FAB): m/Z 560 (M+H, 60%), 365 (8%), 337 (M-side chain, 18%), 196 (Ph$_2$CO, 45%), 164 (MeOPhCH$_2$N(Me)CH$_2$, 45%), 121 (MeOPhCH$_2$, 100%).

NMR (CDCl$_3$, 400 MHz, ppm): δ0.98 (qd, 1H), 1.5–1.6 (m, 3H), 2.25 (br s, 3H), 2.43 (dm, 1H), 2.53 (t, 1H), 2.77 (tt, 1H), 2.84 (td, 1H), 3.25–3.35 (m, 1H), 3.3–3.43 (m, 1H), 2.56 (d, 1H), 3.61 (s, 3H), 3.78 (s, 3H), 3.80 (br d, 1H), 4.79 (d, 1H), 6.84 (app t, 2H), 7.03 (d, 4H), 7.05–7.10 (m, 1H), 7.11 (t, 2H), 7.15–7.30 (m, 6H).
Step D:

Trans 1-(N,N-diphenylaminocarbonyl)-2-(RS)-(2-(N-(2methoxybenzyl)-N-methylamino)ethylaminocarbonyl) piperidin-4-(RS)-carboxylic acid A solution of 0.044 g (0.078 mmole) of trans methyl 1-(N,N-diphenylaminocarbonyl)-2-(RS)-(2-(N-(2-methoxybenzyl)-N-methylamino)ethylaminocarbonyl)piperidine-4.(RS)-carboxylate (from Example 2, Step C above) in 1 mL of THF was treated with 0.7 mL of water and then 0.032 mL of a 2.5N aqueous solution of sodium hydroxide. The mixture was stirred for 20 hr, treated with 1 drop of 2N aqueous hydrochloric acid, and the volatiles were removed in a stream of nitrogen. The mixture was further concentrated under high vacuum and the residue was carried on immediately in Example 10.
Step E:

Trans 1-(N,N-diphenylaminocarbonyl)-2-(RS)-(2-(N-(2methoxybenzyl)-N-methylamino) ethylaminocarbonyl)-4(RS)-(N,N-dipentylaminocarbonyl)piperidine To a solution of 0.043 g (0.079 mmole) of trans 1-(N,N-diphenylaminocarbonyl)-2-(RS)-(2-(N-(2-methoxybenzyl)-N-methyolamino)ethylamino carbonyl) piperidine-4-(RS)-carboxylic acid (from Example 2, Step D above) and 0.012 g (0.087 mmole) of HOBt in 2.5 mL of dry methylene chloride under nitrogen at 0 deg C. was added 0.021 g (0.11 mmole) of EDAC. The bath was removed and the mixture was allowed to stir at room temperature for 35 min, at which point 0.032 mL (0.158 mmole) of di-n-pentylamine was added and the mixture was allowed to stir for 12 hr. The volatiles were removed in a stream of nitrogen and the residue was purified by flash chromatography on 16 g of silica eluting with 400 mL of 4:100 methanol:methylene chloride, to give 49 mg (91%) of an oil.

Mass Spectrum (FAB): m/Z 684 (M+H, 65%), 196 (Ph$_2$CO, 35%), 164 (MeOPhCH$_2$N(Me)CH$_2$, 45%), 121 (MeOPhCH$_2$, 100%).

NMR (CDCl$_3$, 400 MHz, ppm): δ0.86 (t, 6H), 1.1–1.35 (m, 10H),1.38–1.65 (m, 6H), 2.19 (d, 1H), 2.26 (s, 3H), 2.53 (br t, 2H), 2.82 (td, 1H), 2.85–2.95 (m, 1H), 3.0–3.15 (m, 2H), 3.25–3.63 (m, 5H), 3.79 (s, 3H), 3.81 (d, 1H), 4.81 (d, 1H), 6.80–6.88 (m, 2H), 7.03 (d, 4H), 7.08–7.35 (m, 9H).

EXAMPLE 3

Trans 1-(N,N-diphenylaminocarbonyl)-2-(RS)-(2-(N-(aminocarbonylmethyl)amino)ethylaminocarbonyl)-4-(RS)-(N,N-dipentylaminocarbonyl)piperidine Step A:

N-(t-Butoxycarbonyl)ethylenediamine

To a solution of 1.65 g (27.5 mmole) of ethylenediamine in 20 mL of CH$_2$Cl$_2$ was added a solution of 2.00 g (9.16 mmole) of di-t-butyl dicarbonate in 8 mL of CH$_2$Cl$_2$ dropwise over 20 min at room temperature. After 48 hours, the mixture was filtered and the filtrate concentrated in vacuo to give 1.4 g of an oil.

$^1$H NMR (CDCl$_3$, 200 MHz, ppm): δ1.13 (br s, 2H), 1.42 (s, 9H), 2.77 (t, 2H), 3.15 (q, 2H), 4.85 (v br s, 1H).

Step B:

N-(t-Butoxycarbonyl)-N'-(benzyloxycarbonyl)-N'-(aminocarbonylmethyl)ethylenediamine To a solution of 1.25 g (7.8 mmole) of N-(t-Butoxycarbonyl)ethylenediamine in 10 mL of acetonitrile was added 1.36 mL (7.8 mole) of DIEA followed by 1.44 g (7.8 mmole) of iodoacetamide at room temperature. After 90 min most of the solvent was removed in vacuo and the residue was taken up in 12 mL of $CH_2Cl_2$ and was treated with 1.36 mL (7.8 mmole) of DIEA and then 1.1 mL (7.8 mmole) of benzyl chloroformate. The resulting solution was stirred at room temperature for 2 days, and was then concentrated partly in vacuo. The residue was treated with 100 mL of ethyl acetate and 20 mL of 1M aqueous tartaric acid and the layers were separated. The organic layer was washed with 2×15 mL of water, the tartaric acid layer was extracted with 30 mL of ethyl acetate, this extract was washed with 2×10 mL of water, and the combined organic layers were dried over sodium sulfate, filtered and concentrated in vacuo. The residue was purified by flash chromatography on 131 g of silica gel eluting with 2.5 L of 100:4 $CH_2Cl_2$:methanol to provide 1.5 g (55%) of an oil.

Mass Spectrum (FAB): m/Z 352 (M+H, 5%), 296 (M-isobutylene=H, 8%), 252 (M-isobutylene–$CO_2$ +H, 100%).

$^1$H NMR ($CDCl_3$, 400 MHz, ppm): δ1.40 (s, 9H), 3.29 (br s, 2H), 3.45 (t, 2H), 3.9 (s, 2H), 5.12 (s, 2H), 5.1–5.3 (br d, 1H), 5.59 (br s, 1H), 6.1–6.35 (br m, 1H), 7.25–7.35 (br m, 5H).

Step C:

N-(benzyloxycarbonyl)—N-(aminocarbonylmethyl)ethylenediamin trifluoroacetic acid salt A mixture of 0.16 g (0.46 mmole) of N-(t-Butoxycarbonyl)-N'-(benzyloxycarbonyl)-N'-(aminocarbonylmethyl)ethylenediamine and 0.4 mL of anisole was treated at 0° C. with 2 mL of ice cold trifluoroacetic acid under nitrogen. After 90 min at 0° C., the solution was concentrated in vacuo employing a high vacuum pump and with the heating bath at 48° C. for several hours. The resulting oil was employed directly in Step D below.

Step D:

Trans 1-(N,N-diphenylaminocarbonyl)-2-(RS)-(2-(N-(benzyloxycarbonyl) -N-(aminocarbonylmethyl)amino)ethyaminocarbonyl)-4-(RS)-(N,N-dipentylamino-carbonyl)piperidine A solution of 0.076 g (0.15 mmole) of trans 1-(N,N-diphenylaminocarbonyl)-4-(RS)-(N,N-dipentylaminocarbonyl)piperidine -2-(RS)-carboxylic acid (from Example 1, Step E above) and 0.022 g (0.165 mmole) of HOBt in 6 mL of dry methylene chloride at 0 deg C. under nitrogen was treated with 0.04 g (0.21 mmole) of EDAC. The cooling bath was removed and after 40 min a mixture of 0.11 g (0.3 mmole) of N-(benzyloxycarbonyl)-N-(aminocarbonylmethyl)ethylenediamine trifluoroacetic acid salt (from Example 3, Step C above) and 0.042 mL (0.3 mmole) of triethylamine in 2 mL of methylene chloride was added, and the resulting solution was stirred for 19 hr at room temperature. The mixture was then concentrated in vacuo and the residue partitioned between 20 mL of water and 30 mL of ethyl acetate. The layers were separated and the aqueous layer was extracted with 25 mL of ethyl acetate. The combined organic layers were dried over sodium sulphate, filtered and concentrated in vacuo. The residue was purified by flash chromatography on 36 g of silica eluting with 1 L of 3:100 methanol:methylene chloride then 250 mL of 4:100 methanol:methylene chloride to give 56 mg (50%) of an oil.

Mass Spectrum (FAB): m/Z 764 (M+Na, 1%), 742 (M+H, 1%), 726 (M-$NH_2$+H, 1%), 491 (55%), 462 (35%), 196 ($Ph_2$NCO, 100%), 168 ($Ph_2$N, 50%).

NMR ($CDCl_3$, 400 MHz, ppm): δ0.87 (t, 6H), 1.05–1.35 (m, 10H), 1.4–1.65 (m, 6H), 2.0–2.2 (br s, 1H), 2.78–2.95 (m, 2H), 3.0–3.15 (m, 2H), 3.25–3.6 (m, 6H), 3.70 (br d, 1H), 3.90 (br s, 2H), 4.55–4.8 (br m, 1H), 5.0–5.2 (br s, 2H), 5.3–5.7 (br m, 1H), 6.1–6.3 (br m, 1H), 7.0–7.15 (br m, 3H), 7.13 (t, 2H), 7.25–7.4 (m, 9H), 7.59 (br s, 1H).

Step E:

Trans 1-(N,N-diphenylaminocarbonyl)-2-(RS)-(2-(N-(aminocarbonylmethyl)amino)ethylaminocarbonyl)-4-(RS)-(N,N-dipentylaminocarbonyl)piperidine A solution of 0.055 g (0.074 mmole) of trans 1-(N,N-diphenylaminocarbonyl)-2-(RS)-(2-(N-(benzyloxycarbonyl)-N-(aminocarbonylmethyl)amino)ethylaminocarbonyl)-4-(RS)-(N,N-dipentylaminocarbonyl)piperidine (prepared in Example 3, Step D above) in 5 mL of ethanol was treated with 32 mg of 10% palladium on carbon and the resulting slurry was then stirred under an atmosphere of hydrogen for 3 hr. The mixture was then filtered through a cake of Celite, the cake was washed with 100 mL of ethanol, and the filtrate was concentrated in vacuo, to give 39 mg (87%) of an oil.

Mass Spectrum (FAB): m/Z 608 (M+H, 60%), 491 (95%), 463 (60%), 196 ($Ph_2$NCO, 100%), 168 ($Ph_2$N, 60%). NMR ($CDCl_3$, 400 MHz, ppm): δ0.88 (app q, 6H), 1.05–1.35 (m, 11H), 1.4–1.7 (m, 5H), 2.15 (d, 1H), 2.7–2.93 (m, 2H), 3.0–3.2 (m, 3H) 3.25–3.6 (m, 5H), 3.74 (d, 1H), 4.77 (d, 1H), 5.16 (br s, 1H), 7.04 (d, 4H), 7.05–7.15 (m, 1H), 7.17 (t, 2H), 7.3–7.4 (t, 4H), 7.89 (br t, 1H).

EXAMPLE 4

Trans 1-(N,N-diphenylaminocarbonyl)-2-(RS)-(2-(N-(2-methoxybenzyl) -(N-(aminocarbonylmethyl)amino)ethylaminocarbonyl)-4-(RS)(N,,N-dipentylaminocarbonyl)piperidine A solution of 0.027 g (0.044 mmole) of trans 1-(N,N-diphenylaminocarbonyl)-2-(RS)-(2-(N-(aminocarbonylmethyl)amino)-ethylaminocarbonyl)-4-(RS)-(N ,N-dipentylaminocarbonyl)piperidine (from Example 3, Step E above) and 0.011 mL (0.062 mmole) of DIEA in 1 mL of acetonitrile was treated with 0.014 mL (0.058 mmole) of a 50 wt % solution of 2-methoxybenzyl chloride in chloroform. The mixture was stirred at room temperature for 18 hr, then at 50 deg C. for 11 hr and then at 70 deg C. for 48 hr more. The mixture was cooled and concentrated in vacuo, and the residue was purified by flash chromatography on 16 g of silica eluting with 3:100 methanol:methylene chloride to give 23 mg (72%) of an oil.

Mass Spectrum (FAB): m/Z 727 (M+H, 45%), 491 (35%), 462 (40%), 196 ($Ph_2$NCO, 60%), 168 ($Ph_2$N, 40%).

NMR ($CDCl_3$, 400 MHz, ppm): δ0.85 (to, 6H), 1.05–1.35 (m, 10H), 1.44 (pentet, J=7.4, 3H), 1.5–1.65 (m, 3H), 2.10 (d, J=13.4, 1H), 2.60 (t, J=5.6, 2H), 2.81 (td, J=12.9, 2.3, 1H), 3.0–3.3 (m, 6H), 3.35–3.6 (m, 3H), 3.68 (app d, J=3.3, 2H), 3.73 (d, J=13.5, 1H), 3.76 (s, 3H), 4.64 (d, J=4.8, 1H), 4.88 (d, J=2.7, 1H), 6.84–6.9 (m, 2H), 7.04 (app d, J=7.5, 4H), 7.15–7.25 (m, 4H), 7.33 (app t, J=8.3, 5H), 7.70 (br t, 1H).

EXAMPLE 5

Cis 1-(N,N-diphenylaminocarbonyl)-2-(RS)-(2-(N-(2-methoxybenzyl)-N-methylamino)ethylaminocarbonyl)-4-(SR)-(N,N-dipentylaminocarbonyl)piperidine Step A:

Racemic cis and trans methyl 1-(N,N-diphenylaminocarbonyl)-4-(N,N-dipentylaminocarbonyl)piperidine-2carboxylate A solution of 0.375 g (0.72 mmole) of a 2:1 mixture of cis:trans methyl 1-(N,N-diphenylaminocarbonyl)piperidine-4-carboxylic acid-2-carboxylate (from Example 2, Step A) and 0.011 mL (0.072 mmole) of DBU in 6 mL of methylene chloride was stirred at room temperature under nitrogen for 36 hr. The mixture was treated with an additional 0.033 mL of DBU and was heated at reflux for 14 hr. The solvent was removed in a stream of nitrogen and the residue was dissolved in 7 mL of toluene, and the resulting mixture was heated at 6 hr at 90 deg C., at 110 deg C. for 14 hr and at 120 deg C. for 24 hr. The mixture was cooled to room temperature and was concentrated in vacuo, and the residue was partly purified by flash chromatography on 68 g of silica eluting with 1.5 L of 66:33 hexanes: ethyl acetate and then 700 mL of 4:100:0.15 methanol:methylene chloride:acetic acid, to give trans methyl 1-(N,N-diphenylaminocarbonyl)-4-(RS)-(N,N-dipentylaminocarbonyl)piperidine-2-(RS)-carboxylate as the major component and cis methyl 1-(N,N-diphenylaminocarbonyl)-4-(RS) (N,N-dipentylaminocarbonyl)piperidine-2-(SR)-carboxylate as the minor component. Final purification of the latter material was carried out by flash chromatography on 36 g of silica eluting with 1.1 L 75:25 hexanes:ethyl acetate to give 25 mg of cis methyl 1-(N,N-diphenyl-aminocarbonyl)-4-(RS)-(N,N-dipentylaminocarbonyl)piperidine-2-(SR) carboxylate.

NMR (CDCl$_3$, 400 MHz, ppm): δ0.86 (t, 3H), 0.89 (t, 3H), 1.15–1.35 (m, 8H), 1.38–1.65 (m, 6H), 1.95 (dt, 1H), 2.03–2.13 (to, 1H), 2.5–2.6 (m, 1H), 3.1–3.25 (m, 5H), 3.48–3.55 (m, 1H), 3.72 (s, 3H), 4.22 (dd, 1H), 7.09–7.16 (m, 5H), 7.25–7.30 (m, 5H).

Step B:

Cis 1-(N,N-diphenylaminocarbonyl)-4-(RS)-(N,N-dipentylaminocarbonyl)piperidine-2-(SR)-carboxylic acid A solution of 0.025 g (0.048 mmole) of cis methyl 1-(N,N-diphenylaminocarbonyl)-4-(RS)-(N ,N-dipentylaminocarbonyl)-piperidine-2-(SR)-carboxylate in 1 mL of THF and 0.7 mL of water was treated with 0.019 mL of aqueous 10% sodium hydroxide, and the mixture was stirred at room temperature for 24 hr. The solution was treated with 1 drop of 2N aqueous hydrochloric acid and the volatiles were removed with a vigorous stream of nitrogen. The residual white solid was carded on in Step C below.

Step C:

Cis 1-(N,N-diphenylaminocarbonyl)-2-(RS)-(2-(N-(2methoxybenzyl)—N-methylamino)ethylaminocarbonyl)-4(SR)-(N,N-dipentylaminocarbonyl)piperidine A solution of 0.024 g (0.047 mmole) of crude cis 1-(N,N-diphenylaminocarbonyl)-4-(RS)-(N,N-dipentylaminocarbonyl)-piperidine-2-(SR)-carboxylic acid (from Example 5, Step B) and 0.007 g (0.052 mmole) of HOBt in 1 mL of dry methylene chloride was cooled to 0 deg C. under an atmosphere of nitrogen and the mixture was treated with 0.013 g (0.066 mmole) of EDAC. The cooling bath was removed and after 30 min 0.018 g (0.095 mmole) of N-(2-Methoxybenzyl) -N-methylethylenediamine (from Example 2, Step B) in 1 mL of methylene chloride was added, and the mixture was stirred at room temperature for 20 hr. The reaction mixture was then purified by flash chromatography on 16 g of silica eluting with 450 mL of 4:100:0.1 methanol:methylene chloride:concentrated aqueous ammonia then 5:100:0.1 methanol:methylene chloride:concentrated aqueous ammonia to give 25 mg (78%) of an oil.

Mass Spectrum (FAB): m/Z 684 (M+H, 80%), 462 (25%), 196 (Ph$_2$NCO, 60%), 168 (Ph$_2$N, 30%), 121 (MeOPhCH$_2$, 100%). NMR (CDCl$_3$, 400 MHz, ppm): δ0.84 (t, 3H), 0.92 (t, 3H), 1.15–1.6 (m, 14H), 1.87 (dt, 1H), 2.1, 2.25 (m, 5H), 2.53 (br s, 3H), 3.06–3.65 (m, 9H, 3.79 (s, 3H), 4.10 (dd, 1H), 6.50 (br s, 1H), 6.84–7.0 (m, 2H), 7.05–7.15 (m, 6H), 7.18–7.26 (m, 6H).

EXAMPLE 6

Trans 1-(N-(3-chlorophenyl)-N-(phenyl)-aminocarbonyl)-4-(RS)-(N,N-dipentylaminocarbonyl)piperidine-2-(RS)-carboxylic acid Step A:

N-(3-chlorophenyl)-N-phenylcarbamoyl chloride

A solution of 20.4 g (100 mmole) of commercial 3chlorodiphenylamine in 40 mL of toluene and 100 mL of 1.93M phosgene in toluene were combined and heated at 90 deg C. under nitrogen for 2 hrs with stirring. The red-orange solution was cooled, flushed with nitrogen for 2 hrs to remove excess phosgene and concentrated in vacuo to provide 15.4 g (58%) of a red-orange oil which was homogeneous by TLC (4:1 hexanes:ethyl acetate, Rf=0.8).

Mass Spectrum (FAB): m/Z 266 (M–H).

IR (neat): 1740 cm$^{-1}$, no NH absorption.

Step B:

Cis dimethyl 1-(N-(3-chlorophenyl)—N-(phenyl) aminocarbony)piperidine-2-(RS)4-(SR)-dicarboxylate A solution of 0.159 g (0.79 mmole) of cis dimethyl piperidine-2-(RS),4-(SR)-dicarboxylate (from Example 1, Step A above) and 0.263 g (1 mmole) of N-(3-chlorophenyl)-N-phenylcarbamoyl chloride in 3 mL of dry methylene chloride was treated with 0.131 mL (0.95 mmole) of triethylamine, and the mixture was stirred at room temperature for 24 hr and at reflux for 86 hr. The mixture was purified by flash chromatography on 36 g of silica eluting with 1 L of 75:25 hexanes:ethyl acetate to give 335 mg (98%) of an oil.

NMR (CDCl$_3$, 400 MHz, ppm): δ1.5–1.7 (dm, 2H), 2.0–2.1 (m, 1H), 2.13–2.2 (m, 1H), 2.54 (pentet, 1H), 3.28–3.38 (m, 1H), 3.41 (dd, 1H), 3.63 (s, 3H), 3.72 (s, 3H), 4.44 (t, 1H), 6.98 (dd, 1H), 7.05–7.25 (m, 6H), 7.33 (app t, 2H).

Step C:

Trans methyl 1-(N-(3-chlorophenyl)-N-(phenyl)-aminocarbonyl)piperidine-2-(RS)-carboxylic acid-4-(RS)-carboxylate and trans methyl 1-(N-(3-chlorophenyl)-N(phenyl)-aminocarbonyl)piperidine-4-(RS)-carboxylic acid-2-(RS)-carboxylate A solution of 0.325 g (0.75 mmole) of cis dimethyl 1-(N(3-chlorophenyl)-N-(phenyl)-aminocarbonyl)piperidine-2-(RS),4-(SR)-dicarboxylate in 6 mL of methanol was treated with a solution of 0.050 g (0.75 mmole) of 85% potassium hydroxide in 2 mL of methanol, and the resulting mixture was stirred at room temperature for 68 hr at which point 4 drops of water was added and the mixture stirred for an additional 96 hr. The reaction was then treated with 2N aqueous hydrochloric acid until the pH was 3.5 and the mixture was concentrated in vacuo. The residue was purified by flash chromatography on 130 g of silica eluting with 3 L of 2:100:0.2 methanol:methylene chloride:acetic acid to give 143 mg (45%) of higher Rf material (trans methyl 1-(N-(3-chlorophenyl)-N-(phenyl)-aminocarbonyl)piperidine-4-(RS)-carboxylic acid-2-(RS)-carboxylate) and 114 mg (36%) of lower Rf material (trans methyl 1-(N-(3-chlorophenyl)—N-(phenyl)-aminocarbonyl)piperidine-2-(RS)-carboxylic acid-4-(RS)-carboxylate). Proton NMR evaluation revealed that the higher Rf compound was a 9:1 trans:cis mixture.

NMR (CDCl$_3$, 400 MHz, ppm): δ for higher Rf component: 1.35 (qd, 1H), 1.6–1.7 (m, 1H), 1.81 (br d, 1H), 2.35–2.45 (m, 2H), 2.92 (td, 1H), 3.77 (s, 3H), 3.86 (br d, 1H), 5.00 (br s, 1H), 6.93 (dd, 1H), 7.0–7.25 (m, 6H), 7.33 (app t, 2H); for lower Rf component: 1.20 (qd, 1H), 1.64 (td, 1H), 1.71 (br d, 1H), 2.42 (br d, 1H), 2.51 (tt, 1H), 3.96 (td, 1H), 3.64 (s, 3H), 3.78 (br d, 1H), 4.92 (br d, 1H), 6.96 (dd, 1H), 7.03–7.23 (m, 6H), 7.33 (app t, 2H).

Step D:

Trans methyl 1-(N-(3-chlorophenyl)-N-(phenyl)-aminocarbonyl)-4-(RS)-(N,N-dipentylaminocarbonyl)piperidine-2-(RS)-carboxylate A solution of 0.140 g (0.34 mmole) of trans methyl 1-(N(3-chlorophenyl) -N-(phenyl)-aminocarbonyl)piperidine-4-(RS)-carboxylic acid-2-(RS)-carboxylate and 0.050 g (0.37 mmole) of HOBt in 5 mL of dry methylene chloride was cooled to 0 deg C. under nitrogen and was treated with 0,090 g (0.047 mmole) of EDAC. The cooling bath was removed and after 40 min 0.135 mL (0.67 mmole) of di-n-pentylamine was added, and the mixture was stirred at room temperature for 24 hr. The mixture was concentrated in vacuo and the residue partly purified by flash chromatography on 35 g of silica eluting with 900 mL of 1:100 methanol:methylene chloride. Final purification was carried out by flash chromatography on 68 g of silica eluting with 2 L of 80:20 hexanes:ethyl acetate and then 600 mL of 67:33 hexanes: ethyl acetate to give 144 mg (77%) of a clear oil.

Mass Spectrum (FAB): m/Z 557 (M+H, 20%), 325 (M–ClPhN(Ph)CO, 100%), 230 (ClPhN(Ph)CO, 25%), 140 (50%).

NMR (CDCl$_3$, 400 MHz, ppm): δ0.8–0.9 (to, 6H), 1.15–1.35 (m, 9H), 1.4–1.8 (m, 6H), 2.13 (br d, 1H), 2.50 (tt, 1H), 2.84 (td, 1H), 3.1–3.35 (m, 4H), 3.78 (s, 3H), 3.86 (br d, 1H), 5.03 (br s, 1H), 6.94 (dd, 1H), 7.0–7.25 (m, 6H), 7.33 (app t, 2H).

Step E:

Trans 1-(N-(3-chlorophenyl)-N-(phenyl)-aminocarbonyl)-4-(RS)-(N,N-dipentylaminocarbonyl)piperidine-2-(RS)-carboxylic acid A solution of 0.144 g (0.26 mmole) of trans methyl 1-(N(3-chlorophenyl)-N-(phenyl)-aminocarbonyl)-4-(RS)-(N,N-dipenty aminocarbonyl)piperidine-2-(RS)-carboxylate in 3 mL of THF was treated with 2.5 mL of water and then 0.104 mL of a 2.5N aqueous solution of sodium hydroxide, and the mixture was stirred at room temperature for 14 hr. The reaction mixture was treated with 2N aqueous hydrochloric acid, 6 mL water and methylene chloride/ethyl acetate, the layers were separated, and the aqueous layer was extracted with 2x20 mL of ethyl acetate. The organic extracts were dried over magnesium sulfate, filtered and concentrated in vacuo. The residue was purified by flash chromatography on 36 g of silica eluting with 1 L of 2.5:100:0.1 methanol:methylene chloride:acetic acid, to give 130 mg (93%) of a viscous oil.

Mass Spectrum (FAB): m/Z 543 (M+H, 35%), 267 (100%), 230 (ClPhN(Ph)CO, 55%), 204 (55%), 158 (50%).

NMR (CDCl$_3$, 400 MHz, ppm): δ0.8–0.9 (m, 6H), 1.15–1.35 (m, 9H), 1.45 (pentet, 4H), 1.5–1.6 (m, 1H), 1.74 (td, 1H), 2.17 (d, 1H), 2.8–2.95 (2H), 3.1–3.2 (m, 2H), 3.3–3.45 (m, 2H), 3.72 (d, 1H), 4.83 (d, 1H), 6.99 (dd, 1H), 7.05 (m, 1H), 7.09–7.17 (m, 3H), 7.2–7.3 (m, 2H), 7.38 (app t, 2H).

EXAMPLE 7

Trans 1-(N-(3-chlorophenyl)-N-(phenyl)-aminocarbonyl)-2-(RS)-(2-(N(2-methoxybenzyl)-N-methylamino)ethylaminocarbonyl)-4-(RS)-(N,N-dipentylaminocarbonyl)piperidine Step A:

Trans methyl 1-(N-(3-chlorophenyl)-N-(phenyl)aminocarbonyl)-2-(RS)-(2-(N-(2-methoxybenzyl)-N-methylamino)ethylaminocarbonyl)piperidine-4-(RS)-carboxylate A suspension of 0.112 g (0.27 mmole) of trans methyl 1-(N -(3-chlorophenyl)-N-(phenyl)-aminocarbonyl)piperidine-2-(RS)carboxylic acid-4-(RS)-carboxylate (from Example 6, Step C) in 6 mL of methylene chloride was treated with 1 mL of acetonitrile and 0.040 g (0.29 mmole) of HOBt. The mixture was cooled to 0 deg C. and was treated with 0.072 g (0.38 mmole) of EDAC. The cooling bath was removed, the mixture was stirred for an additional 35 min and then 0.104 g (0.54 mmole)of N-(2-methoxybenzyl)- N-methylethylenediamine (from Example 2, Step B) was added and the reaction was stirred for 16 hr. The solution was partly concentrated and the residue was purified by flash chromatography on 16 g of silica eluting with 300 mL of 3.5:100 methanol:methylene chloride then 200 mL of 5:100 methanol:methylene chloride to give 108 mg (68%) of an oil.

Mass Spectrum (FAB): m/Z 593 (M+H, 100%), 164 (20%), 122 (MeOPhCH$_2$+H, 50% ).

NMR (CDCl$_3$, 400 MHz, ppm): δ0.99 (qd, 1H), 1.5–1.6 (m, 2H), 2.25 (br s, 3H), (2.41 (dd, 1H), 1.5–1.6 (m, 2H), 2.76 (tt, 1H), 2.88 (td, 1H), 3.25–3.35 (m, 1H), 3.4–3.5 (m, 1H), 3.5–3.6 (m, 2H), 3.61 (s, 3H), 3. (br d, 1H), 3.79 (s, 3H), 4.78 (d, 1H), 6.8–6.95 (m, 3H), 6.95–7.22 (m, 7H), 7.25–7.35 (m, 3H).

Step B:

Trans 1-(N-(3-chlorophenyl)-N-(phenyl)-aminocarbonyl)-2-(RS)-(2-(N-(2-methoxybenzyl)-N-methylamino)-ethylaminocarbonyl)piperidine-4-(RS)-carboxylic acid A solution of 0.108 g (0.18 mmole) of trans methyl 1-(N-(3-chlorophenyl)-N-(phenyl)-aminocarbonyl)-2-(RS)-(2-(N-(2-methoxybenzyl)-N-methylamino)ethylaminocarbonyl)piperidine-4-(RS)carboxylate in 2.2 mL of dry THF was treated with 1.5 mL of water and then 0.073 mL of a 2.5N aqueous solution of sodium hydroxide, and the mixture was stirred at room temperature for 15 hr. The mixture was concentrated partly in a vigorous stream of nitrogen and partly in vacuo, and was used as is in further reactions.

Step C:

Trans 1-(N-(3-chlorophenyl)-N-(phenyl)-aminocarbonyl)-2-(RS)-(2-(N-(2-methoxybenzyl)-N-methylamino)ethylaminocarbonyl)-4-(RS)-(N,N-dipentylamino-carbonyl)piperidine According to the procedure given in Example 2, Step E, 0.051 g of trans 1-(N-(3-chlorophenyl)- N-(phenyl)-aminocarbonyl)-2-(RS) -(2-(N-(2-methoxybenzyl)-N-methylamino)ethylaminocarbonyl)-piperidine-4-(RS)-carboxylic acid gave 43 mg (68%) of an oil.

Mass Spectrum (FAB): m/Z 719 (M+H, 45%), 230 (ClPhN(CO)Ph, 20%), 164 (MeOPhCH$_2$N(Me)CH$_2$, 35%), 121 (MeOPhCH$_2$, 100%).

NMR (CDCl$_3$, 400 MHz, ppm): δ0.86 (t, 6H), 1.15–1.65 (m, 16H), 2.17 (d, 1H), 2.27 (br s, 3H), 2.5–2.6 (m, 2H), 2.7–2.95 (m, 2H), 3.0– 3.15 (m, 2H), 3.25–3.7 (m, 5H), 3.78 (br d, 1H), 3.79 (s, 3H), 4.81 (d, 1H), 6.8–6.96 (m, 3H), 7–7.35 (m, 10H).

EXAMPLE 8

Trans 1-(N-(3-chlorophenyl)-N-(phenyl)-aminocarbonyl)-2-(RS)-(2-(N(2-methoxybenzyl)-N-methylamino)ethylaminocarbonyl)-4-(RS)-(N,N-dibenzylaminocarbonyl)piperidine According to the procedure given in Example 2, Step E, 0.051 g of trans 1-(N-(3-chlorophenyl)-N-(phenyl)-aminocarbonyl)-2-(RS)-(2-(N-(2-methoxybenzyl)-N-methylamino)ethylaminocarbonyl)-piperidine-4-(RS)-carboxylic acid and 0.035 g of dibenzylamine gave 22 mg (33%) of an oil.

Mass Spectrum (FAB): m/Z 759 (M+H, 10%), 230 (ClPhN(CO)Ph, 10%), 164 (MeOPhCH$_2$N(Me)CH$_2$, 30%), 121 (MeOPhCH$_2$, 100%).

NMR (CDCl$_3$, 400 MHz, ppm): δ1.37 (qd, 1H), 1.69 (td, 2H), 2.11 (br s, 3H), 2.33 (br d, 1H), 2.48 (br t, 2H), 2.75 (td, 1H), 3.05 (tt, 1H), 3.2–3.3 (m, 1H), 3.35–3.45 (m, 1H), 3.47–3.60 (m, 2H), 3.74 (br d, 1H), 3.76 (s, 3H), 4.07 (d, 1H), 4.33 (d, 1H), 4.82 (d, 1H), 4.83 (br d, 1H), 4.97 (d, 1H), 6.78–6.85 (m, 2H), 6.92 (d, 1H), 7.05–7.35 (m, 20H).

EXAMPLE 9

Trans 1-(N-(3-chlorophenyl)-N-(phenyl)-aminocarbonyl)-2-(RS)-(2-(N-(benzyloxycarbonyl) -N-(aminocarbonylmethyl)amino)ethylaminocarbonyl)-4-(RS)-(N,N-dipentylaminocarbonyl)piperidine According to the procedure given in Example 3, Step D, 0.11 g of trans 1-(N-(3-chlorophenyl)-N-(phenyl)-aminocarbonyl)-4-(RS) -(N,N-dipentylaminocarbonyl)piperidine-2-(RS)-carboxylic acid (from Example 6, Step E above) gave 69 mg (44%) of the product, along with 49 mg of recovered starting material.

Mass Spectrum (FAB): m/Z 776 (M+H, 5%), 573 (30%), 525 (100%), 497 (45%), 293 (65%), 267 (75%), 230 (95%), 167 (55%), 158 (60%). NMR (CDCl$_3$, 400 MHz, ppm): most signals broadened due to rotomers δ0.83–0.93 (m, 6H), 1–1.7 (m, 18H), 2–2.2 (br m, 1H), 2.8–2.9 (m, 2H), 3.05–3.15 (m, 2H), 3.2–3.7 (m, 6H), 3.8–4.0 (m, 2H), 4.6–4.8 1H), 5–5.2 (m, 2H), 5.3–5.5 (m, 1H), 6.1–6.2 (br s, 1H), 6.94 (d, 1 7.05–7.15 (m, 3H), 3.15–7.4 (m, 10H), 7.5–7.65 (m, 1H).

EXAMPLE 10

Trans 1-(N-(3-chlorophenyl)-N-(phenyl)-aminocarbonyl)-2-(RS)-(2-N-(aminocarbonylmethyl)amino) ethylaminocarbonyl) 4-(RS)-(N,N-dipentylaminocarbonyl)piperidine A mixture of 0.069 g (0.089 mmole) of trans 1-(N-(3-chlorophenyl) -N-(phenyl)-aminocarbonyl)-2-(RS)-(2-(N-(benzyloxycarbonyl)-N -(aminocarbonylmethyl)amino)ethylaminocarbonyl)-4-(RS)-(N,N-dipentylaminocarbonyl)piperidine (from Example 9) and 5 mL of a 30% solution of HBr in acetic acid was stirred at room temperature for 1 hr under a drying tube. Nitrogen was bubbled through the mixture for 2 hr to remove HBr and the mixture was concentrated in vacuo. The residue was treated with methylene chloride, methanol and aqueous ammonia, and the mixture was purified by flash chromatography on 36 g of silica eluting with 1 L of 4:100 methanol: methylene chloride, then 500 mL of 5:100 methanol:methylene chloride to give 33 mg (58%) of an oil.

NMR (CDCl$_3$, 400 MHz, ppm): δ0.8–0.9 (m, 6H), 1.15–1.35 (m, 8H), 1.4–1.7 (m, 8H), 2.17 (d, 1H), 2.7–2.9 (m, 3H), 3–3.6 (m, 8H), 3.72 (d, 1H), 4.74 (d, 1H), 5.03 (s, 1H), 6.9–7.5 (m, 9H), 7.81 (t, 1H).

EXAMPLE 11

Trans 1-(N-(3-chlorophenyl)-N-(phenyl)-aminocarbonyl)-2-(RS)-(2-(N(2-methoxybenzyl) -N-(aminocarbonylmethyl)amino)ethylaminocarbonyl)-4-(RS)-(N,N-dipentylaminocarbonyl)piperidine According to the procedure in Example 4, 0.016 g (0.025 mmole) of trans 1-(N-(3-chlorophenyl)-N-(phenyl)-aminocarbonyl)-2-(RS)-( 2-N-(aminocarbonylmethyl)amino)ethylaminocarbonyl)-4-(RS)-(N,N-dipentylaminocarbonyl)piperidine gave 15 mg (79%) of an oil.

Mass Spectrum (FAB): m/Z 762 (M+H, 16%), 525 (8%), 497 (8%), 293 (15%), 230 (17%), 121 (100%).

NMR (CDCl$_3$, 400 MHz, ppm): δ0.8–0.9 (m, 6H), 1.1–1.35 (m, 10H), 1.4–1.65 (m, 8H), 2.09 (d, 1H), 2.60 (t, 2H), 2.8–2.9 (1H), 3–3.2 (m, 6H), 3.2–3.3 (m, 1H), 3.3–3.6 (m, 3H), 3.6–3.75 (m, 3H), 3.77 (s, 3H 4.64 (d, 1H), 5.00 (d, 1H), 6.85–6.95 (m, 4H), 7.04 (app d, 1H), 7.1–7.3 (m, 5H), 7.3–7.4 (2H), 7.53 (br t, 1H).

EXAMPLE 12

Typical Pharmaceutical Compositions Containing a Compound of the Invention
A: Dry Filled Capsules Containing 50 mg of Active Ingredient
Per Capsule

| Ingredient | Amount per capsule (mg) |
|---|---|
| Active ingredient | 50 |
| Lactose | 149 |
| Magnesium stearate | 1 |
| Capsule (size No. 1) | 200 |

The active ingredient can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.
B: Tablet
A typical tablet would contain the active ingredient (25 mg), pregelatinized starch USP (82 mg), microcrystalline cellulose (82 mg) and magnesium stearate (1 mg).
C: Suppository
Typical suppository formulations for rectal administration contain the active ingredient (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Direction
A typical injectible formulation contains the acting ingredient sodium phosphate dibasic anhydrous (11.4 mg), benzyl alcohol (0.01 ml) and water for injection (1.0 ml).
While the invention has been described and illustrated with reference to certain particular embodiments thereof, those skilled in the an will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carders, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula:

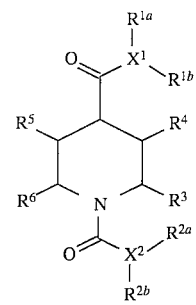

or a pharmaceutically acceptable salt thereof, wherein:
  $R^{1a}$ is selected from the group consisting of:
   1) H,
   2) $C_{1-8}$ alkyl,
   3) phenyl, either unsubstituted or substituted with one or two substituents selected from the group consisting of:
     a) —$C_{1-4}$ alkyl,
     b) -halo,
     c) —OH,
     d) —$CF_3$,
     e) —$NH_2$,
     f) —NH($C_{1-4}$ alkyl),
     g) —N($C_{1-4}$ alkyl)($C_{1-4}$ alkyl),
     h) —$CO_2H$,
     i) —$CO_2$($C_{1-4}$ alkyl), and
     j) —$C_{1-4}$ alkoxy;
   4) —$C_{1-4}$alkyl-phenyl, wherein the phenyl is either unsubstituted or substituted with one or two substituents selected from:
     a) —$C_{1-4}$ alkyl,
     b) -halo,
     e) —OH,
     d) —$CF_3$
     e) —$NH_2$,
     f) —NH($C_{1-4}$ alkyl),
     g) —N($C_{1-4}$ alkyl)$_2$,
     h) —$CO_2H$,
     i) —$CO_2$($C_{1-4}$ alkyl), and
     j) —$C_{1-4}$ alkoxy;
  $R^{1b}$ is selected from the group consisting of:
   1) $R^{1a}$
   2) —$C_{3-7}$ cycloalkyl, and
   3) —$CH_2$—$R^{1a}$;
  $R^{2a}$ and $R^{2b}$ are independently phenyl, either unsubstituted or substituted with one or two substituents selected from the group consisting of:
   1) —$C_{1-4}$ alkoxy,
   2) -halo,
   3) —OH,
   4) —$CF_3$,
   5) —$NH_2$,
   6) —NH($C_{1-4}$ alkyl),
   7) —N($C_{1-4}$ alkyl)$_2$,
   8) —$CO_2H$,
   9) —$CO_2$($C_{1-4}$ alkyl), and
   10) —$C_{1-6}$ alkyl, either unsubstituted or substituted with one or more substituents selected from the group consisting of:
     a) -halo,
     b) —OH,
     c) —$CF_3$,
     d) —$NH_2$, c) —NH($C_{1-4}$ alkyl),
f) —N($C_{1-4}$ alkyl)($C_{1-4}$ alkyl)
g) —$CO_2H$,
h) —$CO_2$($C_{1-4}$ alkyl),
i) $C_{1-4}$alkoxy,
j) —S(O)$_x$($C_{1-4}$ alkyl) wherein x is 0, 1 or 2,
k) —$C_{3-7}$ cycloalkyl;

and the phenyl groups of $R^{2a}$ and $R^{2b}$ may be joined together at the ortho carbon atoms through a carbon-carbon single bond or $C_{1-3}$ alkylene to form a tricyclic group with the $X^2$ to which they are attached;

$X^1$ is —N, —CH or O, and if $X^1$ is O, $R^{1a}$ is absent;
$X^2$ is —N or —CH;
$R^3$ is selected from the group consisting of:
1) —$CONR^7R^8$, and
2) —$CO_2R^9$;

$R^4$, $R^5$ and $R^6$ are H or are independently selected from the definitions of $R^3$;

$R^7$ is $C_{1-6}$ alkyl substituted with one or more substituents selected from the group consisting of:
1) —$NHR^{10}$,
2) —$NR^{10}R^{11}$,
3) —NHCO($C_{1-6}$alkyl),
4) —$NR^{10}CO_2R^{11}$,
5) —$N(R^{10})((C_{1-6}$ alkyl)$CONHR^{11}$),
6) —$N(CO_2R^{10})((C_{1-6}$alkyl)$CONHR^{11}$), and
7) —$NR^{10}(C_{1-6}$ alkyl)$CONHR^{11}$;

$R^8$ is H, $C_{1-6}$ alkyl or is independently selected from the definitions of $R^7$;

$R^9$ is H or —$CH_2$-phenyl, wherein the phenyl is either unsubstituted or substituted with one or more substituents selected from the group consisting of:
1) —$C_{1-4}$ alkoxy,
2) -halo,
3) —OH,
4) —$CF_3$,
5) —$NH_2$,
6) —NH($C_{1-4}$ alkyl),
7) —N($C_{1-4}$ alkyl)$_2$,
8) —$CO_2H$,
9) —$CO_2$($C_{1-4}$ alkyl), and
10) —$C_{1-6}$ alkyl, either unsubstituted or substituted with one or more substituents selected from the group consisting of:
a) -halo,
b) —OH,
c) —$CF_3$,
d) —$NH_2$,
e) —NH($C_{1-4}$ alkyl),
f) —N($C_{1-4}$ alkyl)($C_{1-4}$ alkyl)
g) —$CO_2H$,
h) —$CO_2$($C_{1-4}$ alkyl),
i) $C_{1-4}$alkoxy,
j) —S(O)$_x$($C_{1-4}$ alkyl) wherein x is 0, 1 or 2,
k) —$C_{3-7}$ cycloalkyl;

$R^{10}$ is H, $C_{1-6}$ alkyl, or —($C_{1-6}$ alkyl)-phenyl, wherein the phenyl is either unsubstituted or substituted with one or more substituents selected from the group consisting of:
1) —$C_{1-4}$ alkoxy,
2) -halo,
3) —OH,
4) —$CF_3$,
5) —$NH_2$,
6) —NH($C_{1-4}$ alkyl),
7) —N($C_{1-4}$ alkyl)$_2$,
8) —$CO_2H$,
9) —$CO_2$($C_{1-4}$ alkyl), and
10) —$C_{1-6}$ alkyl, either unsubstituted or substituted with one or more substituents selected from the group consisting of:
a) -halo,
b) —OH,
c) —$CF_3$,
d) —$NH_2$,
e) —NH($C_{1-4}$ alkyl),
f) —N($C_{1-4}$ alkyl)($C_{1-4}$ alkyl)
g) —$CO_2H$,
h) —$CO_2$($C_{1-4}$ alkyl),
i) $C_{1-4}$alkoxy,
j) —S(O)$_x$($C_{1-4}$ alkyl) wherein x is 0, 1 or 2,
k) —$C_{3-7}$ cycloalkyl; and $R^{11}$ is H, $C_{1-6}$ alkyl, or is independently selected from the definitions of $R^{10}$.

2. The compound of claim 1 wherein $X^1$ and $X^2$ are both N of structural formula:

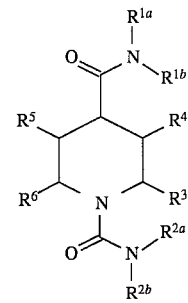

or a pharmaceutically acceptable salt thereof.

3. The compound of claim 2 wherein:
$R^{1a}$ is selected from the group consisting of:
1) $C_{5-6}$ alkyl,
2) phenyl,
3) —$CH_{22}$-phenyl, $R^{1b}$ is selected from the definitions of $R^{1a}$;

$R^{2a}$ and $R^{2b}$ are independently phenyl, either unsubstituted or substituted with one substituent selected from the group consisting of:
1) —$OCH_3$,
2) —Cl,
3) —$CF_3$,
4) —$CH_3$;

$R^3$ is selected from the group consisting of:
1) —$CONR^7R^8$, and
2) —$CO_2R^9$;

$R^7$ is $C_{1-6}$ alkyl substituted with one or more substituents selected from the group consisting of:
1) —$NHR^{10}$,
2) —$NR^{10}OR^{11}$,
3) —NHCO($C_{1-6}$ alkyl),
4) —$NR^{10}CO_2R^{11}$,
5) —$N(CO_2R^{10})((C_{1-6}$ alkyl)$CONHR^{11}$),
6) —$NR^{10}(C_{1-6}$ alkyl)$CONHR^{11}$;

$R^8$ is H, $C_{1-6}$ alkyl or is independently selected from the definitions of $R^7$;

$R^9$ is H or —$CH_2$-phenyl, wherein the phenyl is either unsubstituted or substituted with one or more substituents selected from the group consisting of:
1) —$C_{1-4}$ alkoxy,
2) -halo,
3) —OH, 4) —CF$_3$,
5) —NH$_2$,
6) —NH(C$_{1-4}$ alkyl),
7) —N(C$_{1-4}$ alkyl)$_2$,
8) —CO$_2$H,
9) —CO$_2$(C$_{1-4}$ alkyl), and
10) —C$_{1-6}$ alkyl, either unsubstituted or substituted with one or more substituents selected from the group consisting of:
  a) -halo,
  b) —OH,
  c) —CF$_3$,
  d) —NH$_2$,
  e) —NH(C$_{1-4}$ alkyl),
  f) —N(C$_{1-4}$ alkyl)(C$_{1-4}$ alkyl)
  g) —CO$_2$H,
  h) —CO$_2$(C$_{1-4}$ alkyl),
  i) C$_{1-4}$alkoxy,
  j) —S(O)$_x$(C$_{1-4}$ alkyl) wherein x is 0, 1 or 2,
  k) —C$_{3-7}$ cycloalkyl;

$R^{10}$ is —(C$_{1-4}$ alkyl)-phenyl, wherein the phenyl is either unsubstituted or substituted with one or more substituents selected from the group consisting of:
  1) —OCH$_3$,
  2) —Cl,
  3) —CF$_3$,
  4) —CH$_3$; and $R^{11}$ is H, C$_{1-6}$alkyl, or is independently selected from the definitions of $R^{10}$.

4. The compound of claim 2 wherein:

$R^{1a}$ is selected from the group consisting of:
1) H,
2) C$_{1-8}$ alkyl,
3) phenyl, either unsubstituted or substituted with one or two substituents selected from the group consisting of:
  a) —C$_{1-4}$ alkyl,
  b) -halo,
  c) —OH,
  d) —CF$_3$,
  e) —NH$_2$,
  f) —NH(C$_{1-4}$ alkyl),
  g) —N(C$_{1-4}$ alkyl)(C$_{1-4}$ alkyl),
  h) —CO$_2$H,
  i) —CO$_2$(C$_{1-4}$ alkyl), and
  j) —C$_{1-4}$ alkoxy;
4) —C$_{1-4}$alkyl-phenyl, wherein the phenyl is either unsubstituted or substituted with one or two substituents selected from:
  a) —C$_{1-4}$ alkyl,
  b) -halo,
  e) —OH,
  d) —CF$_3$
  e) —NH$_2$,
  f) —NH(C$_{1-4}$ alkyl),
  g) —N(C$_{1-4}$ alkyl)$_2$,
  h) —CO$_2$H,
  i) —CO$_2$(C$_{1-4}$ alkyl), and
  j) —C$_{1-4}$ alkoxy;

$R^{1b}$ is selected from the group consisting of:
1) $R^{1a}$
2) —C$_{3-7}$ cycloalkyl, and
3) —CH$_2$—$R^{1a}$;

$R^{2a}$ and $R^{2b}$ are independently phenyl, either unsubstituted or substituted with one or two substituents selected from the group consisting of:
1) —C$_{1-4}$ alkoxy,
2) -halo,
3) —OH,
4) —CF$_3$,
5) —NH$_2$,
6) —NH(C$_{1-4}$ alkyl),
7) —N(C$_{1-4}$ alkyl)$_2$,
8) —CO$_2$H,
9) —CO$_2$(C$_{1-4}$ alkyl), and
10) —C$_{1-6}$ alkyl, either unsubstituted or substituted with one or more substituents selected from the group consisting of:
  a) -halo,
  b) —OH,
  c) —CF$_3$,
  d) —NH$_2$,
  e) —NH(C$_{1-4}$ alkyl),
  f) —N(C$_{1-4}$ alkyl)(C$_{1-4}$ alkyl)
  g) —CO$_2$H,
  h) —CO$_2$(C$_{1-4}$ alkyl),
  i) C$_{1-4}$alkoxy,
  j) —S(O)$_x$(C$_{1-4}$ alkyl) wherein x is 0, 1 or 2, and
  k) —C$_{3-7}$ cycloalkyl;

and the phenyl groups of $R^{2a}$ and $R^{2b}$ may be joined together at the ortho carbon atoms through a carbon-carbon single bond or C$_{1-3}$ alkylene to form a tricyclic group with the $X^2$ to which they are attached;

$R^3$ is —CONR$^7$R$^8$;

$R^4$, $R^5$ and $R^6$ are H;

$R^7$ is C$_{1-6}$ alkyl substituted with one or more substituents selected from the group consisting of:
1) —N(R$^{10}$)(CH$_2$CONHR$^{11}$),
2) —N(CO$_2$R$^{10}$)(CH$_2$CONHR$^{11}$), and $R^8$ is H.

5. The compound of claim 2 wherein:

$R^{1a}$ is selected from the group consisting of:
1) H,
2) C$_{1-8}$ alkyl,
3) phenyl, either unsubstituted or substituted with one or two substituents selected from the group consisting of:
  a) —C$_{1-4}$ alkyl,
  b) -halo,
  c) —OH,
  d) —CF$_3$,
  e) —NH$_2$,
  f) —NH(C$_{1-4}$ alkyl),
  g) —N(C$_{1-4}$ alkyl)(C$_{1-4}$ alkyl),
  h) —CO$_2$H,
  i) —CO$_2$(C$_{1-4}$ alkyl), and
  j) —C$_{1-4}$ alkoxy;
4) —C$_{1-4}$alkyl-phenyl, wherein the phenyl is either unsubstituted or substituted with one or two substituents selected from:
  a) —C$_{1-4}$ alkyl,
  b) -halo,
  e) —OH,
  d) —CF$_3$
  e) —NH$_2$,
  f) —NH(C$_{1-4}$ alkyl),
  g) —N(C$_{1-4}$ alkyl)$_2$,
  h) —CO$_2$H,
  i) —CO$_2$(C$_{1-4}$ alkyl), and
  j) —C$_{1-4}$ alkoxy;

$R^{1b}$ is selected from the group consisting of:
1) $R^{1a}$

2) —C$_{3-7}$ cycloalkyl, and
3) —CH$_2$—R$^{1a}$;

R$^{2a}$ and R$^{2b}$ are independently phenyl, either unsubstituted or substituted with one or two substituents selected from the group consisting of:
  1) —C$_{1-4}$ alkoxy,
  2) -halo,
  3) —OH,
  4) —CF$_3$,
  5) —NH$_2$,
  6) —NH(C$_{1-4}$ alkyl),
  7) —N(C$_{1-4}$ alkyl)$_2$,
  8) —CO$_2$H,
  9) —CO$_2$(C$_{1-4}$ alkyl), and
  10) —C$_{1-6}$ alkyl, either unsubstituted or substituted with one or more substituents selected from the group consisting of:
    a) -halo,
    b) —OH,
    c) —CF$_3$,
    d) —NH$_2$,
    e) —NH(C$_{1-4}$ alkyl),
    f) —N(C$_{1-4}$ alkyl)(C$_{1-4}$ alkyl)
    g) —CO$_2$H,
    h) —CO$_2$(C$_{1-4}$ alkyl),
    i) C$_{1-4}$alkoxy,
    j) —S(O)$_x$(C$_{1-4}$ alkyl) wherein x is 0, 1 or 2,
    k) —C$_{3-7}$ cycloalkyl;

and the phenyl groups of R$^{2a}$ and R$^{2b}$ may be joined together at the ortho carbon atoms through a carbon-carbon single bond or C$_{1-3}$ alkylene to form a tricyclic group with the X$^2$ to which they are attached;

R$^3$ is —CONR$^7$R$^8$;

R$^4$, R$^5$ and R$^6$ are H;

R$^7$ is C$_{1-6}$ alkyl substituted with —NR$^{10}$R$^{11}$;

R$^8$ is H;

R$^{10}$ is —(C$_{1-6}$ alkyl)-phenyl, wherein the phenyl is substituted with —C$_{1-4}$ alkoxy, R$^{11}$ is H, C$_{1-6}$ alkyl, or is independently selected from the definitions of R$^{10}$.

6. The compound of claim 2 wherein:

R$^{1a}$ is selected from the group consisting of:
  2) H,
  2) C$_{1-8}$ alkyl,
  3) phenyl, either unsubstituted or substituted with one or two substituents selected from the group consisting of:
    a) —C$_{1-4}$ alkyl,
    b) -halo,
    c) —OH,
    d) —CF$_3$,
    e) —NH$_2$,
    f) —NH(C$_{1-4}$ alkyl),
    g) —N(C$_{1-4}$ alkyl)(C$_{1-4}$ alkyl),
    h) —CO$_2$H,
    i) —CO$_2$(C$_{1-4}$ alkyl), and
    j) —C$_{1-4}$ alkoxy;
  4) —C$_{1-4}$alkyl-phenyl, wherein the phenyl is either unsubstituted or substituted with one or two substituents selected from:
    a) —C$_{1-4}$ alkyl,
    b) -halo,
    e) —OH,
    d) —CF$_3$
    e) —NH$_2$,
    f) —NH(C$_{1-4}$ alkyl),
    g) —N(C$_{1-4}$ alkyl)$_2$,
    h) —CO$_2$H,
    i) —CO$_2$(C$_{1-4}$ alkyl), and
    j) —C$_{1-4}$ alkoxy;

R$^{1b}$ is selected from the group consisting of:
  1) R$^{1a}$
  2) —C$_{3-7}$ cycloalkyl, and
  3) —CH$_2$—R$^{1a}$;

R$^{2a}$ and R$^{2b}$ are independently phenyl, either unsubstituted or substituted with one or two substituents selected from the group consisting of:
  1) —C$_{1-4}$ alkoxy,
  2) -halo,
  3) —OH,
  4) —CF$_3$,
  5) —NH$_2$,
  6) —NH(C$_{1-4}$ alkyl),
  7) —N(C$_{1-4}$ alkyl)$_2$,
  8) —CO$_2$H,
  9) —CO$_2$(C$_{1-4}$ alkyl), and
  10) —C$_{1-6}$alkyl, either unsubstituted or substituted with one or more substituents selected from the group consisting of:
    a) -halo,
    b) —OH,
    c) —CF$_3$,
    d) —NH$_2$,
    e) —NH(C$_{1-4}$ alkyl),
    f) —N(C$_{1-4}$ alkyl)(C$_{1-4}$ alkyl)
    g) —CO$_2$H,
    h) —CO$_2$(C$_{1-4}$ alkyl),
    i) C$_{1-4}$alkoxy,
    j) —S(O)$_x$(C$_{1-4}$ alkyl) wherein x is 0, 1 or 2,
    k) —C$_{3-7}$ cycloalkyl;

and the phenyl groups of R$^{2a}$ and R$^{2b}$ may be joined together at the ortho carbon atoms through a carbon-carbon single bond or C$_{1-3}$ alkylene to form a tricyclic group with the X$^2$ to which they are attached;

R$^3$ is CONR$^7$R$^8$;

R$^4$, R$^5$ and R$^6$ are H;

R$^7$ is C$_{1-6}$ alkyl substituted with —NR$^{10}$R$^{11}$;

R$^8$ is H;

R$^{10}$ is C$_{1-6}$ alkyl;

R$^{11}$ is H or C$_{1-6}$ alkyl.

7. The compound of claim 2 wherein:

R$^{1a}$ is selected from the group consisting of:
  1) H,
  2) C$_{1-8}$ alkyl,
  3) phenyl, either unsubstituted or substituted with one or two substituents selected from the group consisting of:
    a) —C$_{1-4}$ alkyl,
    b) -halo,
    c) —OH,
    d) —CF$_3$,
    e) —NH$_2$,
    f) —NH(C$_{1-4}$ alkyl),
    g) —N(C$_{1-4}$ alkyl)(C$_{1-4}$ alkyl),
    h) —CO$_2$H,
    i) —CO$_2$(C$_{1-4}$ alkyl), and
    j) —C$_{1-4}$ alkoxy;
  4) —C$_{1-4}$alkyl-phenyl, wherein the phenyl is either unsubstituted or substituted with one or two substituents selected from:
    a) —C$_{1-4}$ alkyl,
    b) -halo, c) —OH,
d) —CF$_3$,
e) —NH$_2$,
f) —NH(C$_{1-4}$ alkyl),
g) —N(C$_{1-4}$ alkyl)$_2$,
h) —CO$_2$H,
i) —CO$_2$(C$_{1-4}$ alkyl), and
j) —C$_{1-4}$ alkoxy;

R$^{1b}$ is selected from the group consisting of:
1) R$^{1a}$
2) —C$_{3-7}$ cycloalkyl, and
3) —CH$_2$—R$^{1a}$;

R$^{2a}$ and R$^{2b}$ are independently phenyl, either unsubstituted or substituted with one or two substituents selected from the group consisting of:
1) —C$_{1-4}$ alkoxy,
2) -halo,
3) —OH,
4) —CF$_3$,
5) —NH$_2$,
6) —NH(C$_{1-4}$ alkyl),
7) —N(C$_{1-4}$ alkyl)$_2$,
8) —CO$_2$H,
9) —CO$_2$(C$_{1-4}$ alkyl), and
10) —C$_{1-6}$ alkyl, either unsubstituted or substituted with one or more substituents selected from the group consisting of:
   a) -halo,
   b) —OH,
   c) —CF$_3$,
   d) —NH$_2$,
   e) —NH(C$_{1-4}$ alkyl),
   f) —N(C$_{1-4}$ alkyl)(C$_{1-4}$ alkyl),
   g) —CO$_2$H,
   h) —CO$_2$(C$_{1-4}$ alkyl),
   i) C$_{1-4}$alkoxy,
   j) —S(O)$_x$(C$_{1-4}$ alkyl) wherein x is 0, 1 or 2,
   k) —C$_{3-7}$ cycloalkyl;

and the phenyl groups of R$^{2a}$ and R$^{2b}$ may be joined together at the ortho carbon atoms through a carbon-carbon single bond or C$_{1-3}$ alkylene to form a tricyclic group with the X$^2$ to which they are attached;

R$^3$ is —CO$_2$R$^9$;

R$^4$, R$^5$ and R$^6$ are H;

R$^9$ is H.

8. A compound which is selected from the group consisting of:
1) trans 1-(N,N-diphenylaminocarbonyl)-2-(RS)-(2-(N-(aminocarbonylmethyl)amino)ethylaminocarbonyl)-4-(RS)-(N,N-dipentylaminocarbonyl)piperidine;
2) trans 1-(N,N-diphenylaminocarbonyl)-2-(RS)-(2-(N-(2-methoxybenzyl)-N-(aminocarbonylmethyl)amino)ethylaminocarbonyl)-4-(RS)-(N,N-dipentylaminocarbonyl)piperidine;
3) trans 1-(N-(3-chlorophenyl)-N-(phenyl)-aminocarbonyl)-2-(RS)-(2-(N-(benzyloxycarbonyl)-N-(aminocarbonylmethyl)amino)ethylaminocarbonyl)-4-(RS)-(N,N-dipentylaminocarbonyl)piperidine;
4) trans 1-(N-(3-chlorophenyl)-N-(phenyl)-aminocarbonyl)-2-(RS)-(2-N-(aminocarbonylmethyl)amino)ethylaminocarbonyl)-4-(RS)-(N,N-dipentylaminocarbonyl)piperidine;
5) trans 1-(N-(3-chlorophenyl)-N-(phenyl)-aminocarbonyl)-2-(RS)-(2-(N-(2-methoxybenzyl)-N-aminocarbonylmethyl)amino)ethylaminocarbonyl)-4-(RS)-(N,N-dipentylaminocarbonyl)piperidine;
6) trans 1-(N,N-diphenylaminocarbonyl)-2-(RS)-(2-(N-(2-methoxybenzyl)-N-methylamino)ethylaminocarbonyl)-4-(RS)-(N,N-dipentylaminocarbonyl)piperidine;
7) cis 1-(N,N-diphenylaminocarbonyl)-2-(RS)-(2-(N-(2-methoxybenzyl)-N-methylamino)ethylaminocarbonyl)-4-(SR)-(N,N-dipentylaminocarbonyl)piperidine;
8) trans 1-(N-(3-chlorophenyl)-N-(phenyl)-aminocarbonyl)-2-(RS)-(2-(N-(2-methoxybenzyl)-N-methylamino)ethylaminocarbonyl)-4-(RS)-(N,N-dipentylaminocarbonyl)piperidine;
9) trans 1-(N-(3-chlorophenyl)-N-(phenyl)-aminocarbonyl)-2-(RS)-(2-(N-(2-methoxybenzyl)-N-methylamino)ethylaminocarbonyl)-4-(RS)-(N,N-dibenzylaminocarbonyl)piperidine;
10) trans 1-(N,N-diphenylaminocarbonyl)-2-(RS)-(3-(diethylamino)propylaminocarbonyl)-4-(RS)-(N,N-dipentylaminocarbonyl)piperidine;
11) trans 1-(N,N-diphenylaminocarbonyl)-4-(RS)-(N,N-dipentylaminocarbonyl)piperidine-2-(RS)-carboxylic acid;
12) trans 1-(N-(3-chlorophenyl)-N-(phenyl)-aminocarbonyl)-4-(RS)-(N,N-dipentylaminocarbonyl)piperidine-2-(RS)-carboxylic acid;

or a pharmaceutically acceptable salt thereof.

9. A pharmaceutical composition comprising a pharmaceutically acceptable carder and an effective amount of the compound of claim 1.

10. A method for antagonizing the effect of substance P at its receptor site or for the blockade of neurokinin-1 receptors in a mammal which comprises the administration to the mammal of the compound of claim 1 in an amount that is effective for antagonizing the effect of substance P at its receptor site in the mammal.

* * * * *